(12) United States Patent
Newton et al.

(10) Patent No.: US 12,023,302 B2
(45) Date of Patent: *Jul. 2, 2024

(54) COMPRESSION THERAPY SYSTEM AND METHOD

(71) Applicant: Arjo IP Holding AB, Malmo (SE)

(72) Inventors: Michael David Newton, Boerne, TX (US); Rhys John Morris, Pontypridd (GB)

(73) Assignee: Arjo IP Holding AB, Malmo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/969,141

(22) Filed: Oct. 19, 2022

(65) Prior Publication Data

US 2023/0049622 A1    Feb. 16, 2023

Related U.S. Application Data

(63) Continuation of application No. 16/303,858, filed as application No. PCT/EP2017/062189 on May 19, 2017, now Pat. No. 11,504,294.

(Continued)

(51) Int. Cl.
*A61H 9/00* (2006.01)
*A61B 5/00* (2006.01)
(Continued)

(52) U.S. Cl.
CPC .......... *A61H 9/0078* (2013.01); *A61B 5/4836* (2013.01); *A61B 5/021* (2013.01);
(Continued)

(58) Field of Classification Search
CPC .......... A61H 9/0078; A61H 2201/5002; A61H 2201/5015; A61H 2201/5038;
(Continued)

(56) References Cited

U.S. PATENT DOCUMENTS 5,571,075 A * 11/1996 Bullard ................ A61H 9/0078
601/24
6,080,120 A    6/2000 Sandman et al.
(Continued)

FOREIGN PATENT DOCUMENTS

EP    2436308 A1    4/2012
JP    H11290408 A    10/1999
(Continued)

OTHER PUBLICATIONS

Dr. Mads Haahr, "Introduction to Randomness and Random Numbers," Oct. 14, 2014. (Year: 2014).*

(Continued)

*Primary Examiner* — Justine R Yu
*Assistant Examiner* — Benjamin M. Kusiak
(74) *Attorney, Agent, or Firm* — The Webb Law Firm

(57) ABSTRACT

An apparatus for promoting vascular circulation, including a garment configured to at least partially surround an anatomical structure of a patient. A compression element is coupled to the garment and configured to compress at least a portion of the anatomical structure when the compression element is actuated. A controller is configured to selectively actuate the compression element over a plurality of cycles. Each cycle has an actuated time during which the compression element is arranged to exert a first pressure and an unactuated time during which the compression element is arranged to exert a second pressure different than the first pressure, and the controller is configured to use a random value in determining the deflated time of one or more of the cycles.

14 Claims, 10 Drawing Sheets

Related U.S. Application Data

(60) Provisional application No. 62/341,894, filed on May 26, 2016.

(51) Int. Cl.
*A61B 5/021* (2006.01)
*A61B 5/024* (2006.01)

(52) U.S. Cl.
CPC ...... *A61B 5/024* (2013.01); *A61H 2201/5002* (2013.01); *A61H 2201/5015* (2013.01); *A61H 2201/5038* (2013.01); *A61H 2205/10* (2013.01); *A61H 2209/00* (2013.01)

(58) Field of Classification Search
CPC ............ A61H 2205/10; A61H 2209/00; A61H 2201/165; A61H 9/00; A61H 9/0092; A61H 9/005; A61H 11/00; A61H 11/005; A61H 11/02; A61H 2201/0103; A61B 5/4836; A61B 5/021; A61B 5/024; A61B 5/1123
USPC .................................................. 601/148–152
See application file for complete search history.

(56) References Cited

U.S. PATENT DOCUMENTS

| | | | |
|---|---|---|---|
| 6,884,255 | B1 | 4/2005 | Newton |
| 2002/0035375 | A1* | 3/2002 | Berish .................. A61H 9/0078 606/105 |
| 2005/0070954 | A1 | 3/2005 | Johnson et al. |
| 2005/0187500 | A1* | 8/2005 | Perry .................... A61H 9/0007 601/150 |
| 2005/0235988 | A1* | 10/2005 | Hansen ................... F04B 35/06 128/200.24 |
| 2006/0217643 | A1* | 9/2006 | Yonekawa ........... A61H 9/0078 601/151 |
| 2006/0282026 | A1* | 12/2006 | Glen .................. A61H 23/0218 601/111 |
| 2006/0287621 | A1* | 12/2006 | Atkinson ............. A61H 9/0078 601/151 |
| 2007/0088239 | A1* | 4/2007 | Roth .................... A61H 9/0078 601/152 |
| 2009/0062703 | A1* | 3/2009 | Meyer .................. A61H 9/0078 606/192 |
| 2011/0082401 | A1 | 4/2011 | Iker et al. |
| 2011/0295126 | A1* | 12/2011 | Quinn .................. A61B 5/0225 600/481 |
| 2011/0296621 | A1* | 12/2011 | McKenna .......... A61G 7/05776 5/713 |
| 2012/0065561 | A1* | 3/2012 | Ballas .................. A61H 9/0092 601/152 |
| 2012/0083712 | A1* | 4/2012 | Watson ................ A61B 5/7275 600/587 |
| 2014/0276291 | A1* | 9/2014 | Mansur, Jr. .......... A61H 9/0078 601/152 |
| 2015/0150560 | A1* | 6/2015 | Sato .................... A63B 23/0355 606/202 |
| 2015/0245976 | A1 | 9/2015 | Jackson et al. |
| 2015/0359541 | A1* | 12/2015 | Ross ..................... A61F 13/148 606/203 |
| 2016/0001034 | A1* | 1/2016 | Rembrand ............ A61M 21/02 600/27 |
| 2016/0270948 | A1* | 9/2016 | Hariri .................. A61H 9/0078 |
| 2016/0361224 | A1* | 12/2016 | Ramakrishna ....... A61H 9/0092 |
| 2017/0239131 | A1* | 8/2017 | Brzenchek .......... A47C 21/048 |
| 2018/0177677 | A1* | 6/2018 | Pamplin ................ A61F 13/085 |
| 2018/0185238 | A1 | 7/2018 | Ilan |
| 2019/0083353 | A1* | 3/2019 | Khurana .............. A61H 9/0092 |

FOREIGN PATENT DOCUMENTS

| | | |
|---|---|---|
| JP | 2004261563 A | 9/2004 |
| WO | 03053323 A2 | 7/2003 |
| WO | 2005082314 A1 | 9/2005 |

OTHER PUBLICATIONS

Stack Overflow, "How do I create a list of random numbers without duplicates?", Mar. 2012, accessed from URL: https:// stackoverflow.com/questions/9755538/how-do-i-create-a-list-of-random-numbers-without-duplicates (Year: 2012).*

W3schools, "Python Range() Function," May 25, 2018, accessed from URL: https://www.w3schools.com/python/ref_func_range.asp (Year: 2018).*

Dr. Mads Haahr, "Introduction to Randomness and Random Numbers," Oct. 14, 2014, accessed from the URL: https://www.random.org/randomness/.

Office Action issued in JP2018560806 dated Feb. 25, 2021.

Stack Overflow, "How do I create a list of random numbers without duplicates?", Mar. 2012, accessed from the URL: https://stackoverflow.com/questions/9755538/how-do-i-create-a-list-of-random-numbers-without-duplicates'.

W3schools, "Python Range() Function," 2021, accessed from the URL: https://www.w3schools.com/python/ref_func_range.asp.

* cited by examiner

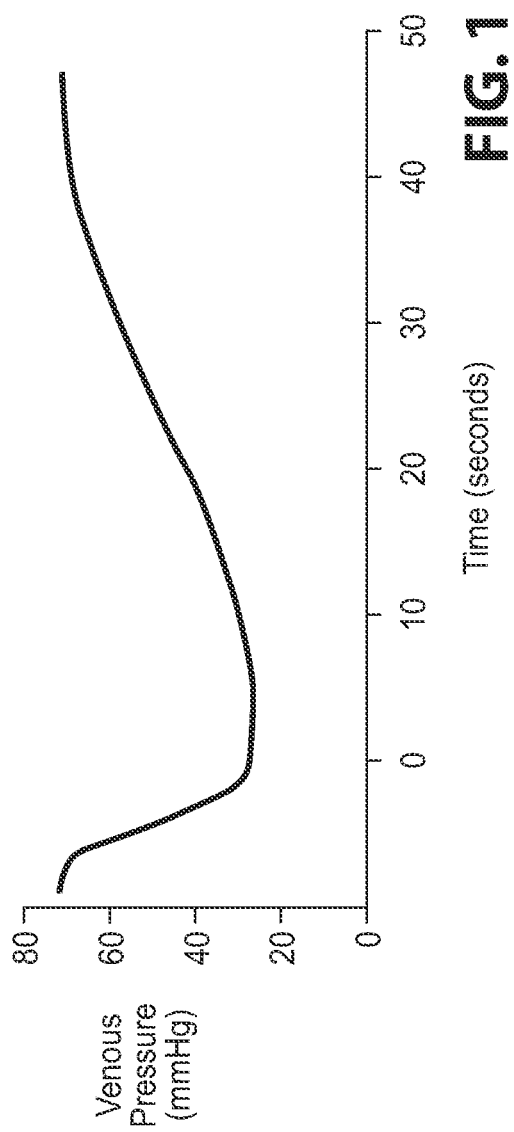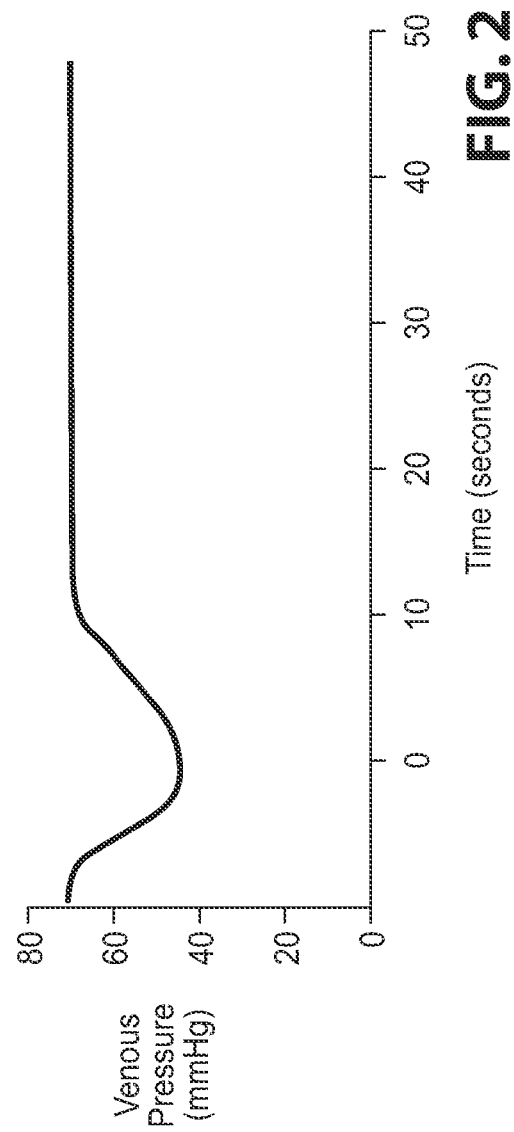

COMPRESSION THERAPY SYSTEM AND METHOD

CROSS REFERENCE TO RELATED APPLICATIONS

This application is a continuation of U.S. patent application Ser. No. 16/303,858, filed Nov. 21, 2018, now U.S. Pat. No. 11,504,294, issued Nov. 22, 2022, which is the United States National Stage of International Patent Application No. PCT/EP2017/062189, filed May 19, 2017, which claims benefit of priority to U.S. Provisional Patent Application No. 62/341,894 filed May 26, 2016, all of which are incorporated by reference in their entireties.

BACKGROUND

Deep vein thrombosis ("DVT") and other adverse medical conditions can occur when blood is stagnant or circulates poorly within the body. For this reason, therapies have been developed to promote blood flow within patients in order increase circulation and reduce the occurrence of DVT and these other conditions. As one example, compression therapy is known in the art and practiced by wrapping a calf, thigh, foot, or other anatomical structure of a patient in an inflatable garment (e.g., sleeve) and cyclically inflating and deflating the garment to force displacement of blood out of the musculature and circulatory vessels within a patient's limb when compressed due to inflation, thereby promoting blood flow within the patient. The veins of the patient refill with blood when the garment is in the deflated part of the cycle.

One goal of such therapies, particularly for bed-ridden or otherwise stationary or movement-impaired patients, is to maximize the volume of blood circulated. However, in the case of compression therapy, each patient may have a different "ideal" or desired time for each inflation-deflation cycle, e.g., patients of different physiologies, ages, injuries, mobility, or health conditions may require in some cases significantly different cycle times. Despite advances in patient monitoring, it remains impractical to accurately or affordably continuously determine each patient's venous refill time for all anatomical areas and therefore provide an optimal form of compression therapy. This is most notably the case when the variation found across the entire patient population is considered and also the associated variation in the circulatory performance of a given patient due to clinical effects/situations. There is always a desire in the medical arts to more effectively, in both cost and result, treat an increasing number of patients of varying physiologies and conditions.

SUMMARY

An apparatus for promoting vascular circulation according to an exemplary embodiment, wherein the apparatus includes a garment configured to at least partially surround an anatomical structure of a patient; a compression element coupled to the garment and configured to compress at least a portion of the anatomical structure when the compression element is actuated; and a controller configured to selectively actuate the compression element over a plurality of cycles; wherein each cycle has an actuated time during which the compression element is arranged to exert a first pressure and an unactuated time during which the compression element is arranged to exert a second pressure different than the first pressure, and the controller is configured to use one or more random values in determining the deflated time of one or more of the cycles.

A pump for inflating an inflatable chamber of a garment according to an exemplary embodiment, wherein the pump includes a controller configured to selectively inflate and deflate the chamber over a plurality of cycles, wherein each cycle has an inflated time and a deflated time, and the controller is configured to assign one or more random values for the deflated times of one or more of the cycles.

An apparatus for providing compression therapy to an anatomic structure of a patient according to an exemplary embodiment, wherein the apparatus includes a compression element configured to exert a first compression pressure and a second compression pressure different than the first compression pressure; a controller configured to selectively actuate the compression element over a plurality of cycles, each cycle having an actuated time during which the compression element is exerting the first compression pressure and an unactuated time during which the compression element is exerting the second compression pressure, wherein the controller constantly variably sets the deflated times for each of the cycles such that the deflated times are not the same for any set of two sequential cycles in the plurality.

A method for using a pump to inflate and/or deflate a chamber of a compression garment configured to be positioned about an anatomic structure according to an exemplary embodiment, wherein the method involves the steps of selectively inflating and/or deflating the chamber over a plurality of cycles, wherein each cycle has an inflated time and a deflated time, and assigning one or more random values for the deflated times of one or more of the cycles.

A method for using a compression apparatus configured to be positioned about an anatomic structure of a person according to an exemplary embodiment, wherein the method involves selectively actuating a compression element over a plurality of cycles, wherein each cycle has an actuated time during which the compression element is exerting a first compression pressure and an unactuated time during which the compression element is exerting a second compression pressure different than the first compression pressure; and variably setting the deflated times for one or more of the cycles such that the deflated times are not the same for two sequential cycles in the plurality of cycles. Optionally, the step of variably setting the deflated times involves using one or more random values in determining the deflated time of the one or more of the cycles.

In any of the embodiments described herein, the one or more random values may be pseudorandomly generated by a mathematical algorithm. In any of the embodiments described herein, the one or more random values may be selected from a pre-generated list of values. In any of the embodiments described herein, the random values may be calculated or determined by the controller in real time during use of the apparatus or pump. In any of the embodiments described herein, the random values may be selected from within a range defined between a minimum limit and a maximum limit. In any of the embodiments described herein, the range of random values may be variable between different cycles. In any of the embodiments described herein, a parameter may be utilized by the controller in determining the range. In any of the embodiments described herein, the parameter may be related to: the anatomical structure; the patient or the patient's condition or status; an ambient environment in which the anatomical structure or the patient is located during use of the apparatus or pump;

another medical device monitoring the patient; a detected type, model, manufacturer, or style of the garment; or a combination including at least one of the foregoing. In any of the embodiments described herein, the apparatuses or pumps may further comprise a sensor for measuring the parameter. In any of the embodiments described herein, the random values for one or more prior cycles may be used by the controller to determine the range for a subsequent cycle. In any of the embodiments described herein, the range of random values may be set by a user of the apparatus or pump. In any of the embodiments described herein, an inflation pressure in a chamber of the apparatus when inflated by the controller may be variable between different cycles. In any of the embodiments described herein, the inflation pressure may be randomly determined by the controller. In any of the embodiments described herein, the inflation pressure for a given cycle may be set by the controller in proportion to the deflation length of: the given cycle, a previous cycle, or a combination including at least one of the foregoing. In any of the embodiments described herein, the controllers may be configured to assign a predetermined value for the deflated time of at least one of the cycles. In any of the embodiments described herein, the controller may be configured to switch between predetermined and randomly determined values in a preset pattern or sequence. In any of the embodiments described herein, the controller may determine a set of random values for a set of cycles and arranges the set of random values in a forced sequence. In any of the embodiments described herein, for a number of cycles the forced sequence may: increase in value; decrease in value; oscillate between relatively greater and relatively lower values; be within a set deviation from a threshold value, a minimum value, or a maximum value; or be a combination thereof including at least one of the foregoing. In any of the embodiments described herein, the anatomical structure may be a calf, a thigh, a foot, a leg, an arm, a hand, an abdomen, a buttocks, a portion of at least one of the foregoing, or combination including at least one of the foregoing. In any of the embodiments described herein, the compression element may include an inflatable chamber. In any of the embodiments described herein, the controller may include or form a part of a pump configured to inflate the chamber. In any of the embodiments described herein, the apparatus or pump may include a rotary valve or a solenoid valve. In any of the embodiments described herein, the controller is configured to be switchable between a first mode in which the random values are selected and a second mode in which the random values are not selected. In any of the embodiments described herein, the controller may be configured to provide the deflated time for each cycle in the plurality of cycles such that the deflated times for any set of two successive cycles are not the same. In any of the embodiments described herein, the maximum limit of a range of random values of the apparatus or pump may be between about 30 seconds and 60 seconds. In any of the embodiments described herein, the maximum limit of a range of random values of the apparatus or pump may be about 48 seconds. In any of the embodiments described herein, the minimum limit of a range of random values of the apparatus or pump may be between about 10 seconds and 40 seconds. In any of the embodiments described herein, the inflation time of the apparatus or pump is about 12 seconds. In any of the embodiments described herein, the inflation pressure of the apparatus or pump is between about 25 mmHg and about 65 mmHg.

BRIEF DESCRIPTION OF THE DRAWINGS

The following descriptions should not be considered limiting in any way. With reference to the accompanying drawings, like elements are numbered alike:

FIG. 1 graphically illustrates venous pressure with respect to time for a representative "normal" patient population over one cycle of compression therapy system;

FIG. 2 graphically illustrates venous pressure with respect to time for a representative patient population having venous reflux over one cycle of compression therapy;

DETAILED DESCRIPTION

A detailed description of one or more embodiments of the disclosed apparatus and method are presented herein by way of exemplification and not limitation with reference to the Figures.

FIGS. 1 and 2 illustrate example plots showing venous pressure in a patient's limb with respect to time for a representative normal healthy patient and a patient having venous reflux, respectively. It is to be understood that each of FIGS. 1 and 2 corresponds to the average results of patients in a hypothetical patient population and that these results are included for the sake of discussion only and not intended to be limiting. A left-hand portion of each plot (when time is less than 0s), shows the venous pressure dropping to a minimum value, such as would occur due to normal use (e.g., exercise) of musculature surrounding the veins being monitored. The pressure drop is the result of the blood within the veins being forced or squeezed out due to use of the surrounding muscles compressing the vein and forcing the blood to circulate. After use of the muscles ceases, the veins again refill with blood, thereby causing the venous pressure to increase back toward a maximum, as illustrated in the right-hand portion of each plot (when time is greater than 0s).

Muscle use or exercise for bed-ridden or otherwise impaired patients is commonly simulated by compression therapy to achieve this same effect, i.e., squeezing veins to force blood to circulate within the body. Accordingly, it is to be appreciated that each of FIGS. 1 and 2 represent one inflation-deflation cycle during compression therapy in which a garment is alternatingly inflated and deflated as discussed above. For ease of discussion, the length of time during a cycle in which the garment is inflated may be referred to herein as the "inflated time", while the length of time during a cycle in which the garment is deflated may be referred to herein as the "deflated time". The amount of time required for a patient's veins to fully refill after compression is referred to herein as the patient's "venous refill time".

As can be appreciated by a comparison of FIGS. 1 and 2, the venous refill time is significantly shorter for patients with venous reflux (e.g., about 10-20s in FIG. 2) than those without (e.g., greater than about 45s in FIG. 1). Despite this disparity in venous refill time, current commercially-available DVT compression therapy systems are typically set with fixed cycle times that are determined by the "normal" refill time represented by FIG. 1. For example, one commonly utilized cycle time is a fixed cycle time of 60 seconds for calf-based compression therapy, in which 12 seconds are utilized for inflation/compression and 48 seconds are utilized for deflation refill. In contrast, a patient having venous reflux may have fully refilled veins in as little as ten or fewer seconds. The fixed cycle time of 60s is used throughout for the sake of convenience in discussion and should not be considered limiting.

Figure 3:
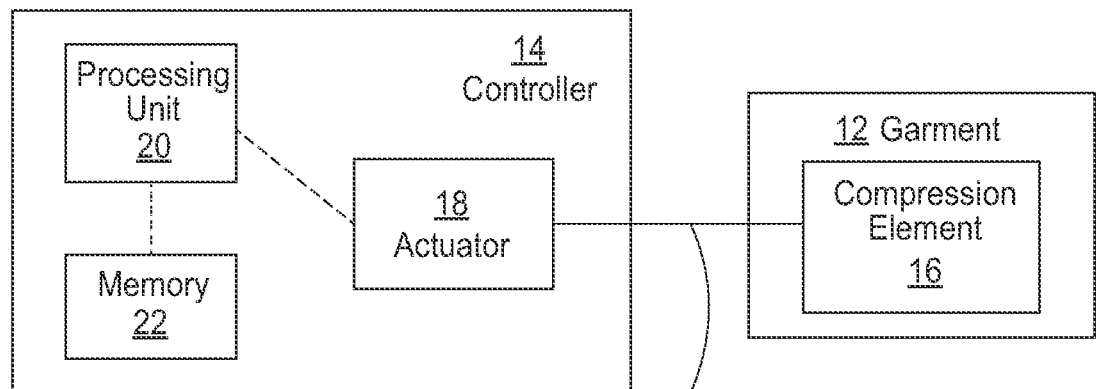
FIG. 3 schematically illustrates a compression therapy system according to one embodiment disclosed herein.

FIG. 3 schematically depicts a flow augmentation system 10. The system 10 may be considered or referred to as a compression therapy system. By augmented and augmentation it is meant that the volumetric flow of vascular fluids in a patient utilizing the system is increased relative to the amount that would have occurred absent the inclusion of a flow augmentation system. In one embodiment, the vascular fluid flow includes blood flow, specifically venous blood flow, although it is to be appreciated that other fluids, such as arterial blood flow, lymphatic fluid flow, etc. are also improved by use of the system 10. For this reason, it is to be understood that any discussion herein with respect to venous blood flow generally also applies to other vascular fluids, as the increased or augmented circulation of many vascular fluids is promoted by the methods herein. In accordance with the above discussion, it is one goal of the system 10 to increase the average amount of augmented blood flow achieved for the largest number of patients within a representative patient population.

The system 10 includes a garment 12 that is connected to a controller 14. The garment 12 includes a compression element 16 that is actuatable via communication (e.g., fluid, electrical, signal, mechanical, etc.) with the controller 14, e.g., via a conduit or linkage 15. The controller 14 is arranged to selectively actuate the compression element 16 to alternatively exert and release pressure on the patient's anatomy and/or otherwise cause the muscle to selectively contract, e.g., by use of an actuator 18 arranged for this purpose. Typically, commercial compression therapy systems include an inflatable chamber that is selectively inflated by a pump. Accordingly, in one embodiment, the actuator 18 may take the form of a pumping mechanism, such as one or more rollers, vanes, gears, screws, scrolls, solenoids or electromagnetic components, diaphragms, rams, plungers, or any other mechanism known or discovered in the art for delivering pressurized fluid. In one embodiment, the compression element 16 includes one or more electrical contacts and compression of the patient's anatomical structure or musculature is accomplished via electrical stimulation, e.g., which causes a patient's musculature to selectively contract. It is envisioned that the entire controller 14 may be contained in a single housing or encasement, or otherwise coupled together in a communicative manner and as such, the controller 14 as a whole may be arranged as or referred to as a "pump" when the compression element 16 is an inflatable chamber and the actuator 18 is or includes a pumping mechanism. Any number and arrangement of valves may additionally or alternatively be included to facilitate inflation and deflation of the compression element 16 when it takes the form of an inflatable chamber. Any desired gas (e.g., ambient air), liquid, or flowable solid (e.g., beads) may be used as the inflation fluid communicable between a pumping mechanism and an inflatable chamber.

However, it is to be appreciated that any number of other mechanism and arrangements exist that are capable of exerting variable pressures on a patient. For example, the compression element 16, conduit or linkage 15, and/or actuator 18 may be arranged as, or include, one or more rollers, cams, fingers, plungers, motors, crankshafts, eccentrically mounted couplings, springs, shape change or shape memory materials (transition between two or more shapes or configurations in response to a specified stimuli, such as heat, light, chemical substance, etc.), piezoelectric actuator, or other components that are selectively or alternatingly driven into physical contact against the patient's anatomy when actuated to exert a first pressure and to disengage from the patient when unactuated to exert a second pressure that is different that the first pressure (and which may be no pressure at all).

Since typical commercial compression therapy systems use the aforementioned inflatable chamber, these alternating actuated/unactuated conditions, for ease of discussion, may be understood to correspond herein to any discussion of "inflation" and "deflation", respectively, even if non-inflatable systems are used. Accordingly, it is to be appreciated that the aforementioned "inflated time" shall also correspond to the actuation time of a compression element (i.e., the "actuated time" and the "inflated time" both interchangeably refer to the time during which the compression element, regardless of construction, is actuated in order to exert an increased force or pressure against a patient), while the aforementioned "deflation time" shall also correspond to the unactuated time of a compression element (i.e., the "unactuated time" and the "deflated time" both interchangeably refer to the time during which the compression element, regardless of construction, is unactuated in order to release or relieve the pressure on the patient).

Additionally, it is to be understood that although the term "unactuated" is used herein, it is to be understood that this term is only used relative to the term "actuated" to generally mean that a lesser pressure is exerted when unactuated in comparison to the pressure exerted when actuated, but that some pressure may still be exerted even when "unactuated" (i.e., the actuator 18 may operate to some lesser degree even when in the unactuated configuration, as the term is used herein). Furthermore, it is noted that the compression element 16 in some embodiments may be arranged to exert a relatively greater pressure when unactuated (e.g., take the form of a spring-loaded or resilient member that by default is arranged to squeeze or exert a pressure) and the actuator 18 is arranged to release or relieve the pressure when actuated (e.g., to push back against a force of the spring-loaded or resilient member, thereby relieving the pressure exerted on the patient), and that these embodiments are within the scope of the instant description and claims.

Figure 4:
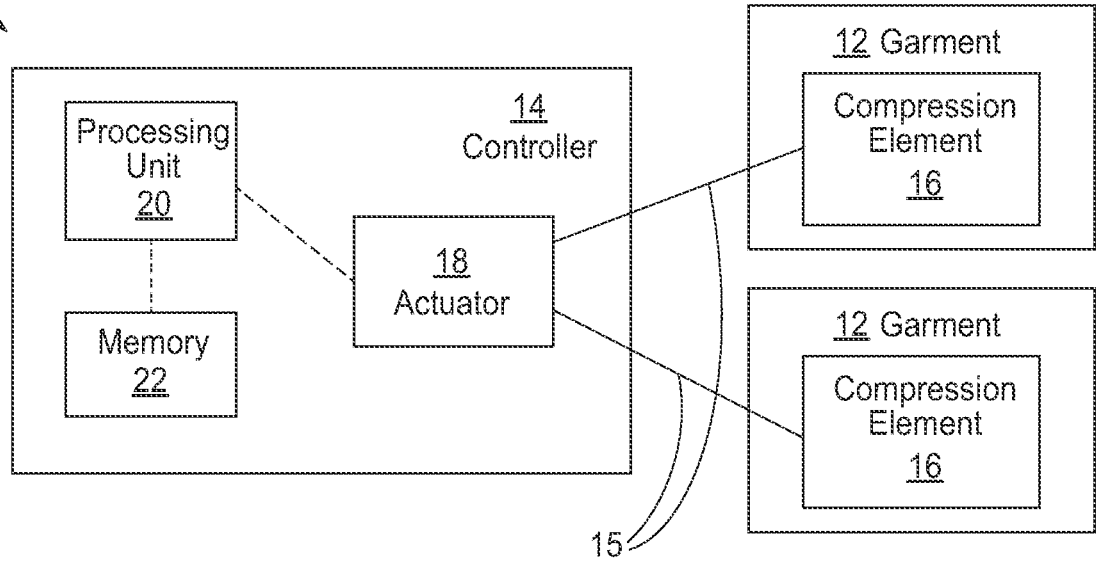
FIG. 4 schematically illustrates a compression therapy system according to another embodiment disclosed herein.

A system 10' is shown in FIG. 4 and generally resembles the system 10 in FIG. 3, including many of the same components. Unlike the system 10, however, the system 10' includes two of the garments 12, each inflatable by the controller 14. For example, the two garments 12 of the embodiment of FIG. 2 may be worn on different areas of the patient, e.g., opposite legs, such that improved treatment can be provided. In one embodiment, the chamber of a first garment is alternatingly inflated while the chamber of a second garment is deflated and vice-versa. Any discussion with respect to the system 10 herein is intended to include the system 10' and any other alternate embodiments disclosed herein and/or appreciated in view of the instant disclosure.

The garment 12 is configured to be at least partially wrapped, secured, or otherwise placed against or about an anatomical structure of a patient, such that alternatingly actuating the compression element 16 will cause the anatomical structure to be repeatedly compressed by the garment 12. It has been well explored in the art that repeated compression of an anatomical structure can promote blood flow in a patient by physically squeezing veins to force blood out of the veins, thereby simulating exercise or muscle use and improving circulation within the patient. This has been found to be particularly useful in patients that are immobile or bed-ridden, and for limbs, e.g., legs, located distally from the heart where blood may otherwise pool and result in health problems such as DVT. It should be appreciated that the anatomical structure may be a foot, calf, thigh, bicep, forearm, chest, abdomen, buttocks, or any other structure in which augmented blood flow is desired and achievable via repeated compression.

Figure 5:
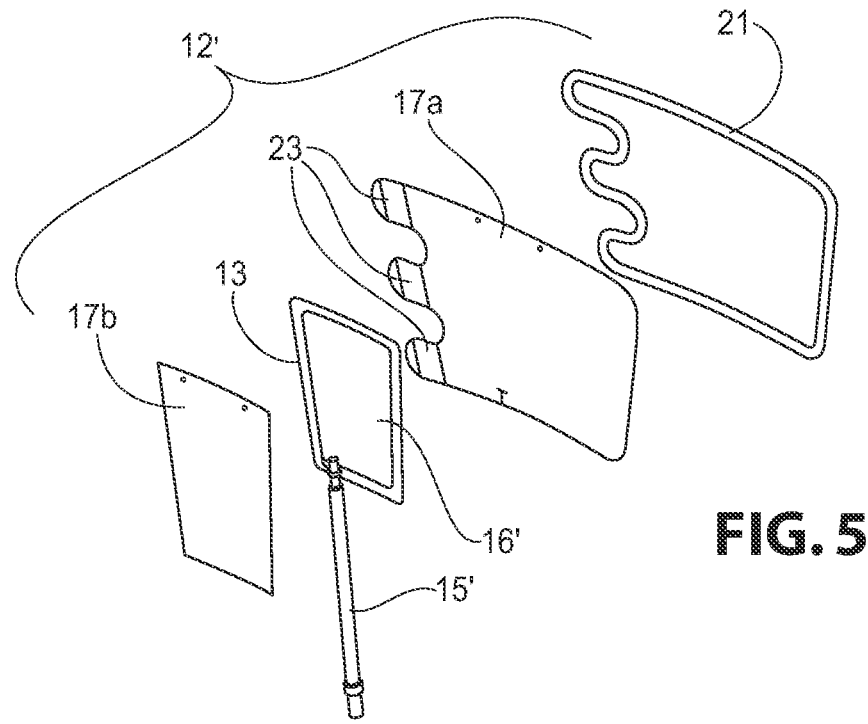
FIG. 5 is an exploded view of a compression garment for a compression therapy system according to one embodiment disclosed herein.

Any number of suitable compression garments are known and used in the art and can be used for or as the garment 12. FIG. 5 illustrates in greater detail an exploded view of a garment 12' according to one non-limiting embodiment (components of the garment 12' generally analogous to those of the garment 12 provided with a prime symbol). The garment 12' includes an inflatable bladder 13 that defines a pressure fluid chamber 16'. Extending from the bladder 13 is a fluid conduit or tube 15' that is connectable to a pump or other fluid pressure source (e.g., the controller 14). The bladder 13 may be held between fabric layers 17a and 17b, which define a body of the garment 12' and are secured to each other in any desired manner, e.g., stitching, adhesives, etc. A perimeter 21 may additionally be included to provide additional strength to the body of the garment 12', and fasteners 23, e.g., in the form of hook and loop material, may be included for attaching the body of the garment 12' to itself when wrapped about an anatomical structure of the patient.

Broadly, the controller 14 is arranged to control the operation of the actuator 18 and actuation of the compression element 16. That is, the controller 14 is utilized to control how long and how often the actuator 18 is in operation, thereby determining the length and timing of pressures exerted during each operational cycle of the system 10. The system 10 can be arranged to operate continuously for any length of time as needed, e.g., hours, days, etc. The compression element 16 may be permitted to passively vent or disengage (depending on particular construction of the compression element 16) when the actuator 18 is not in operation, or the actuator 18 may be arranged to actively withdraw, deflate, or disengage (as applicable, depending on arrangement) the compression element 16 following each inflation.

In the illustrated embodiment of FIG. 3, the controller 14 includes a processing unit 20 and a memory 22. The processing unit 20 may be or include a central processing unit, or any logic unit, microprocessor, microcontroller, or other component known or discovered in the art for performing mathematical operations and/or executing commands. The memory 22 can be or include a hard disk drive, random-access memory, read-only memory, solid state drive, etc., or any type of electronic information storage media capable of storing software, instructions, processes, applications, or programs defining or determining operation of the controller 14. The processing unit 20 and the memory 22 may be contained on a single integrated chip or connected in electronic signal communication as separate components.

More specifically, in accordance with the principles and embodiments disclosed herein, the controller 14 is arranged to constantly variably and/or randomly set, select, pick, or determine the cycle time or deflated time for one or more cycles of the system 10. For the purposes herein, the terms "set", "select", "generate", "determine", etc., are used essentially interchangeably with respect to use of the selected values. By constantly variable, it is meant that no pair of sequential compression cycles has the same length for their deflated times. By random it is generally meant that the value is set, determined, or influenced at least in part by parameters unrelated to the patient's physiology, medical condition, or status. In order to prevent undesired or clinically less valuable outcomes from occurring (e.g., a deflated time that is either undesirably long or short), randomization may be restricted to values within a specific range, i.e., between the bounds of an upper or maximum limit and a lower or minimum limit. That is, the random value is selected from or defined between an upper limit and a lower limit for each cycle. Various embodiments for setting or determining randomness or random values for the cycle time, as well as the upper and lower limits are discussed herein and below.

In some embodiments, the randomness is achieved by a mathematical function, which is carried out by the controller 14. The term random, as used herein, is intended to include semi-random and pseudorandom values, e.g., having a randomized component, or the appearance or inclusion of certain qualities of randomness. For example, most computerized random number generators operate via mathematic functions that are pseudorandom, and therefore meet the definition of random as used herein. Further embodiments for determining random values and/or randomness are disclosed below.

For reasons that will be more thoroughly discussed below, the current inventors have recognized due to any combination of various factors that optimal cycle or optimal deflated time for any given patient population is unlikely to be achieved by a fixed interval, such as the aforementioned 60s cycle/48s deflated time. By "optimal" it is meant the amount of time that results in the greatest amount of augmented blood flow per unit time for a particular patient. Instead of a fixed cycle, by randomizing the cycle or deflated time of a system, such as the system 10 (e.g., between predetermined upper and lower limits), it is actually statistically more likely that the randomized time will be closer to "optimal" for any given patient in a patient population than if a fixed interval were used.

That is, continuing to randomize multiple cycles in sequence will result in a greater number of patients either hitting their optimal venous refill time on some cycles or at least achieving timing closer to their optimal refill times, thereby increasing overall efficiency. Since the time is randomized, no particular group of patients should be disadvantaged, and most patients actually will see an advantage. In this way, randomization can be used to augment a greater volume of blood flow for a given patient population than would be expected with a fixed interval system. In other words, the average augmented blood flow per patient in the given patient population can be increased by use of randomization of the cycle time of a compression therapy system as discussed herein. Moreover, the increase in the average augmented blood flow per patient can be achieved while mitigating any significant negative effects on any appreciable subset of patients in the population.

As noted above, a 48s deflated time is typical in commercial compression therapy systems. However, it is statistically unlikely that any given patient has a venous refill time exactly equal to 48s. That is, the aforementioned 48s deflation interval used in typical commercial compression therapy systems is selected due to it being sufficiently long for the vast majority of patients to achieve full venous refill following the inflation of the system. While this ensures that a good amount of augmented blood flow is achieved each cycle for virtually all patients (since the compression occurs after the vein has completely refilled in virtually all cases), the optimal deflated time for most patients is expected to be less than 48s.

Generally, no fixed interval is expected to represent the optimal deflated time for most patients due to the natural variety in patients' physiologies, medical conditions, and other factors. It is noted that the optimal deflated time for a patient may equal their venous refill time, but cannot possibly exceed that patient's venous refill time. That is, once a patient's veins are full, the maximum possible augmented blood flow for that cycle is already achieved; waiting additional time before compressing after a patient's veins are completely refilled would only reduce the number of cycles per unit time without increasing blood flow per cycle, thereby decreasing efficiency.

It is understood that patients having venous reflux constitute a significant portion of the patient population that would benefit from compression therapy and that these patients have an optimal deflated time much less than those patients that do not have venous reflux (e.g., between about 10-20s for the example patient population represented by FIG. 2 as compared to about 45s or more for the example patient population represented by FIG. 1). Additionally, it is believed by the current inventors that an improved prophylaxis/therapy is possible if the optimal deflated time for the patients is identified as being less than that patient's venous refill time, even for those patients not having venous reflux. More specifically, it is noted that the rate at which the veins refill is nonlinear. Blood refill speed slows exponentially toward the end of each cycle, which is indicated, e.g., in FIGS. 1 and 2, by the venous pressure asymptotically approaching a maximum (it is logically understood that the volume of blood in the vein generally corresponds to the venous pressure depicted in FIGS. 1 and 2). In accordance with the asymptotic venous refill behavior, it is believed that the optimal deflated time for some patients may actually occur at some point before that patient's venous refill time. That is, some patients may benefit from more cycles that have less augmented flow per cycle, as opposed to fewer cycles that have more augmented flow per cycle. In other words, if the cycle time is reduced in length, then the number of cycles per unit time is increased, such that even if less blood flow is being augmented per cycle, the cycles are occurring more frequently and more overall augmented blood flow is achieved over time.

In addition to the above, there are various hemodynamic and hematologic effects of intermittent compression therapy that have been identified, investigated and are published in the medical industry and that are not directly related to the volume of increased blood flow. These include the scouring effect on the vessel walls and valves due to the promoted blood flow as well as the generation of anti-clotting substances within the blood and other chemical and physical effects created by the physical compression of the patient's vessels and musculature. Since some of these aspects are directly associated with the specific act of compression, it is proposed by the current inventors that the act of increasing the number of compressive cycles over a given period of time will result in an augmentation of these additional effects. Accordingly, it is particularly advantageous be able to provide for this improved functionality across all compression garment types, irrespective of the location, construction, or nature of the garment design.

Despite the understanding that patients' optimal deflated time may be less than their venous refill times, it is not currently cost effective or clinically suitable to accurately and continuously measure the amount of augmented blood flow in a patient's limb or other anatomic site that is suitable for compression. Furthermore, each patient's optimal deflated time may change over time (e.g., as a result of activity/movement of the patient, orientation of the patient such as sitting or lying, ambient temperature, nutritional or pharmaceutical intake, etc.). For this reason, each patient's optimal deflated time cannot be readily ascertained, only estimated. Additionally, as discussed above, the optimal deflated time may differ significantly from patient to patient.

Advantageously, the aforementioned randomization utilized by the system 10 and other embodiments disclosed herein, among other benefits, increases the average augmented blood flow for a given patient population without the need for certainty in each patient's optimal deflated time, and while accommodating patient populations with significantly differing optimal deflated times. The constant changes in cycle time due to the randomization techniques described herein help ensure that more effective therapy is provided for more patients, particularly those at the highest risk of DVT related problems, such as those suffering from venous reflux and other medical conditions. Additionally, some patients may benefit mentally or psychologically by use of the currently described systems versus traditional fixed interval systems. That is, fixed interval therapy may be perceived, consciously or subconsciously, as monotonous by some patients especially over particularly long treatment periods, and the randomization may help to break up the predictable nature of the treatment and alleviate annoyances caused by monotony.

Consider, for example, a given patient $P_1$ having an optimal deflated time $t_o$ less than a fixed interval time $t_f$ (that is, assume $t_o < t_f$ for patient $P_1$). If the time $t_f$ is used for every cycle, the timing for each and every cycle for that patient $P_1$ is less efficient by a time equal to $t_f - t_o$. Now consider a randomized time $t_r$, which is less than $t_f$ (that is, assume $t_r$ is selected, e.g., by the controller 14, such that $t_r < t_f$). Three cases can occur for each cycle: $t_r = t_o$ ("scenario 1"); $t_r > t_o$ ("scenario 2"); or $t_r < t_o$ ("scenario 3").

In the event of scenario 1, the optimal efficiency is reached, which is clearly favorable over the fixed interval scheme. In the event of scenario 2, the cycle is again longer than optimal (similar to the use of the fixed time $t_f$), but time is saved with respect to the fixed time $t_f$, and therefore efficiency increased, since if $t_o < t_r < t_f$ then necessarily $t_r - t_o < t_f - t_o$, and that cycle occurs faster in an amount equal to $t_f - t_r$. As described herein, patients having venous reflux should fall most often into this scenario 2, since their optimal deflated time is expected to be considerably less than currently used fixed intervals, and these patients can therefore benefit largely from the improvements in the therapy the disclosed embodiments provide. Therefore, scenarios 1 and 2 are clearly always favorable for the patient $P_1$.

In the case of scenario 3, then the randomized time $t_r$ is occurring at a point of time before the veins are fully refilled (since the optimal refill time $t_o$ logically cannot occur after the venous refill time G for patient $P_1$). Accordingly, there will be a tradeoff between an increase in the number of cycles per unit time achieved by the more frequently-occurring randomized time $t_r$ with its corresponding reduced blood flow associated with this reduced refill opportunity when compared to the volume of venous refill per cycle achieved by a longer fixed time $t_f$.

As a result, it is not readily possible for any given individual cycle time to determine which time, $t_f$ or $t_r$, is more advantageous in comparison to the other with respect to augmented blood flow (e.g., there is the aforementioned tradeoff between more cycles per unit time resulting from the time $t_r$ in this example and the greater volume of blood flow per cycle resulting from the fixed interval $t_f$). However, it is noted that any potential inefficiencies in scenario 3 for the randomized time $t_r$ in comparison to a fixed interval $t_f$ can be mitigated by setting a minimum limit for the randomized time $t_r$ that prevents the randomized time $t_r$ from being too undesirably short (e.g., in one embodiment, by positioning the minimum limit to correspond to the asymptotic portion of the venous refill curve as discussed above with respect to FIGS. 1 and 2).

The volume of blood moved in a prior art system utilizing a longer duration but fixed cycle is therefore related to $t_f$ and $t_o$. Whereas in the currently disclosed embodiments the volume of blood moved is therefore related to the variation between $t_r$ and $t_o$ and the associated improvement in the number of cycles provided over that normally provided by the fixed cycle time $t_f$.

The effect of the currently disclosed embodiments is such that the resulting varying/random selection of the cycle time is such that whilst any individual cycle time $t_r$ for a patient may be sub-optimal compared to an individual patient refill time $t_o$, the next selected cycle time may be more optimal than could be achieved if a fixed and longer cycle time $t_f$ was used that is itself always sub-optimal relative to $t_o$. Hence when all the cycle times are considered in the aggregate over the prolonged duration of a patient therapy there is an improvement achieved in the blood volume moved as a result of the present invention.

In view of the above, now consider an entire patient population of 'n' patients $\{P_1, P_2, P_n\}$ in which the optimal deflated time for the vast majority of patients is less than the fixed time $t_f$ (that is, assume $t_r < t_f$ for all, or essentially all, patients). The patients in this situation are either going to increase efficiency (i.e., when $t_r$ for a cycle triggers either scenario 1 or scenario 2 as described above), or approximately break even with respect to the fixed interval scheme (i.e., when $t_r$ triggers scenario 3 as described above). In this way, the net result of utilizing the randomization techniques described herein is expected to be an increase in total augmented blood flow (and/or average augmented blood flow per patient) for any given patient population with respect to what is expected for commonly used fixed interval systems. Hence, the present invention affords improvements in the wider effectiveness of the product prescribed to a range of patients within a given clinical setting or environment.

It is to be recognized that optimal deflated time as discussed herein is only determined with respect to attempting to maximize the total augmented blood flow, and does not take into account other aspects or considerations that may be beneficial to a patient. For this reason, it may be desirable for some patients, even those with "optimal" deflated times less than their venous refill time (e.g., $t_o < t_v$), to undergo compression therapy where for at least some cycles the actual deflated time is greater than their optimal deflated time to and/or their venous refill time G. Accordingly, in one embodiment, fixed intervals for the deflated time are interspersed among randomized intervals. For example, there may be a fixed interval, e.g., 48s, that is not determined randomly, and used as the deflated time for a known multiple of, e.g., every 'n' number of cycles, with the deflated time for all other cycles being determined randomly.

Figure 6:
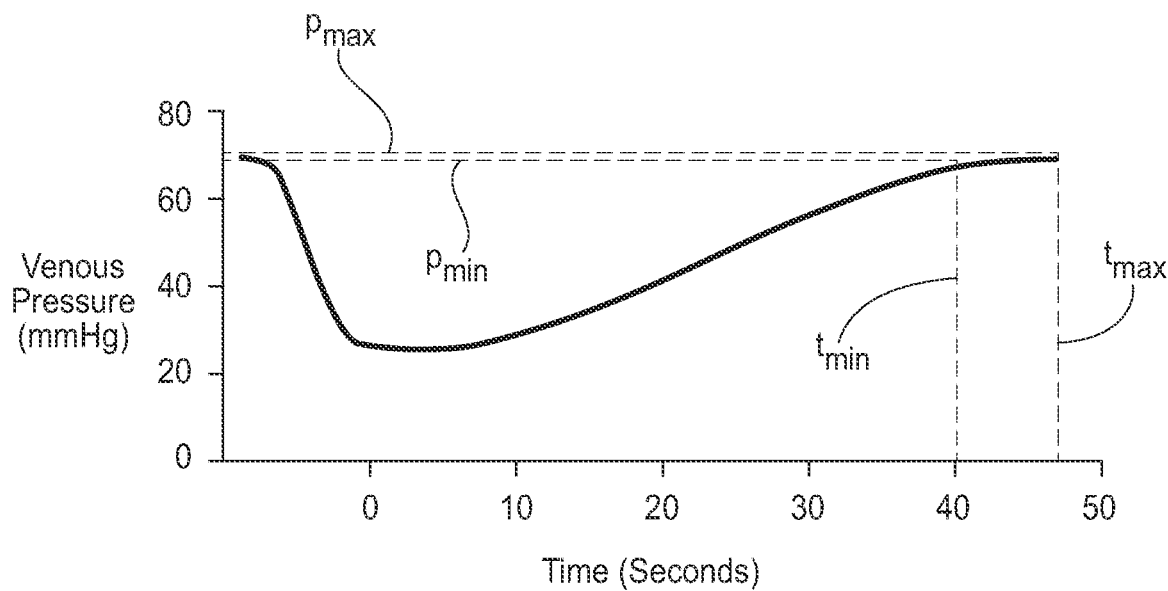
FIG. 6 shows the graph of FIG. 1 annotated to show a minimum and maximum limit for the cycle time.

According to some embodiments, the maximum and minimum limits for the randomization can be selected to span the time period corresponding to the asymptotic end portion of the curve identified in FIGS. 1 and 2, such that a relatively appreciable decrease in deflation length will result in only a fairly negligible decrease in blood refill volume. For example, FIG. 6 is included for the sake of discussing one hypothetical example (that should be in no way considered limiting to the scope of the instant disclosure or claims), which illustrates the same plot as FIG. 1 for "normal" patients, but additionally showing a maximum limit $t_{max}$ for the deflated time set at the typical commercial length of 48s and a representative minimum limit $t_{min}$ set representatively at a time of 40s. Randomly selecting the deflated time as any value between $t_{min}$ and $t_{max}$ (i.e., from the maximum limit of 48s to the minimum limit of 40s as shown in the example of FIG. 6), can in this way be set to result in a corresponding relatively marginal decrease of the volume of refilled blood, i.e., as indicated by the relatively marginal difference between venous pressures $p_{min}$ and $p_{max}$, corresponding to train and $t_{max}$, respectively. Of course, any other maximum and minimum limits may be set in other embodiments, which may result in larger differences between $p_{min}$ and $p_{max}$, but still improve the overall augmented blood flow for the reasons discussed herein.

Figure 9:
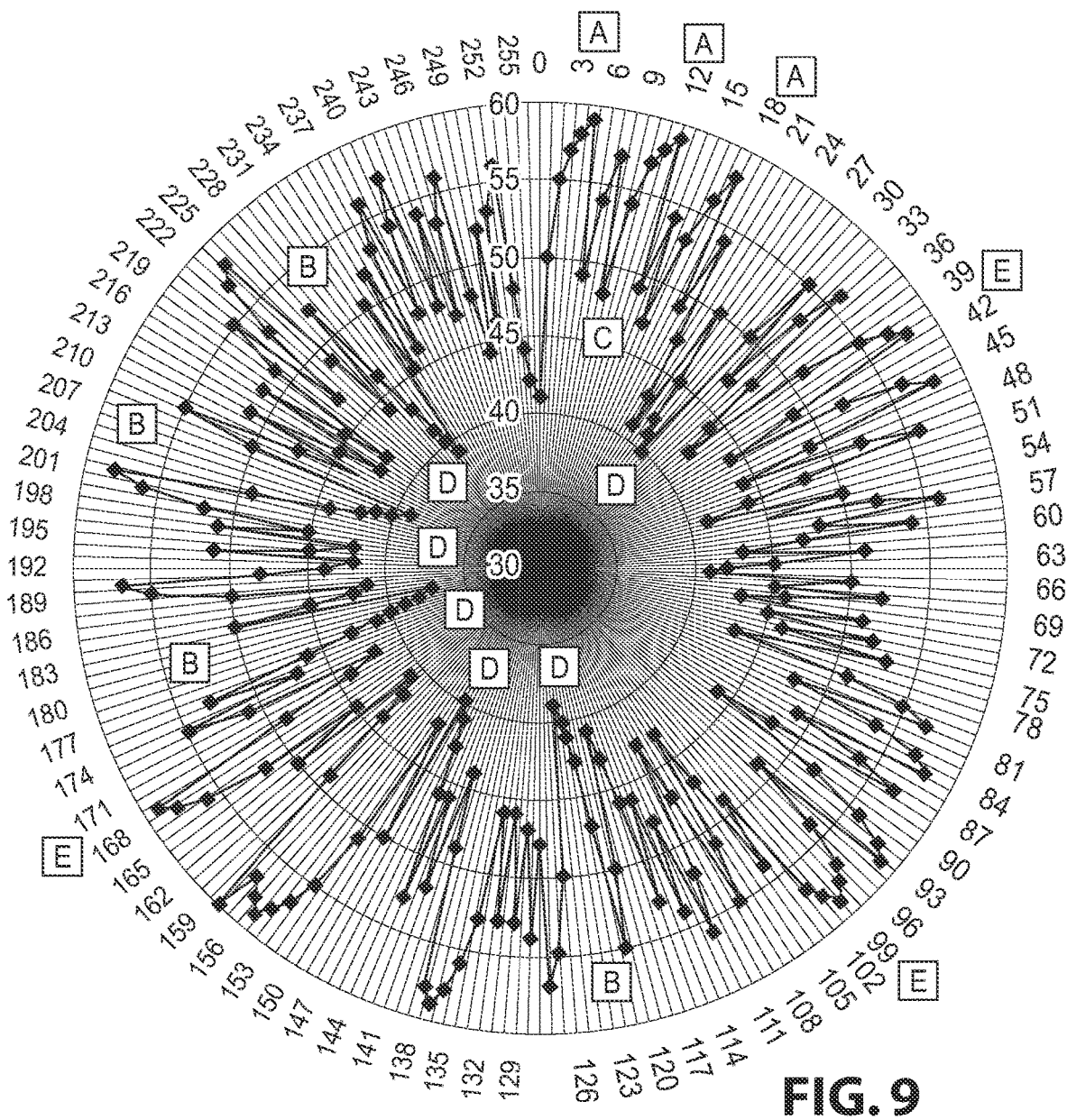
FIG. 9 is a radar plot sequentially illustrating the cycle times for two hundred and fifty-five random compression cycles.

In one embodiment, a user may select various numbers at his/her discretion or based on clinical guidelines to generate a list of random numbers. It is also noted that two or more particular values may be purposely chosen for a particular reason (e.g., selecting a relatively high value and a relatively low value and alternating between the high and the low value). In one embodiment, each number may be generated by random number generator software (e.g., most software programming languages have a "random" or "rand" function), linear sequential shift registers (e.g., see description of FIG. 11), congruence generators, or any other randomization algorithm or sequence generating method. Furthermore, it is noted that the random values may be generated as-needed, on-the-fly, or during the operation of the system 10 (e.g., see description of FIGS. 13 and/or 14), or the random values may be pre-generated or preset and stored into memory (e.g., the memory 22) that is simply read during use of the system 10 (e.g., see description of FIG. 12, and/or FIG. 9 and Table 1).

The generated values can be stored (e.g., in the memory 22) and recalled or displayed (e.g., visually or graphically presented on a monitor, screen or other display; printed; etc.)

or repeated by the system at a later time. In some embodiments, a sequence of two or more numbers is repeated. In some embodiments, a number is selected at random from a list of preset choices for each cycle. In some embodiments, the random number is probabilistically biased toward certain outcomes (i.e., certain outcomes are more likely), while in other embodiments it is unbiased (i.e., each possible outcome is equally likely).

In one embodiment, the controller 14 is prevented from selecting the same value twice in a row. In one embodiment, the deflated time values are arranged in subsets of two or more values and each subset has at least one randomized value, and at least one value determined based on the first value (e.g., via a defined mathematical relationship). For example, a first value may be randomly determined on the fly and a second value determined such that the sum of the first and second numbers equals a desired sum, e.g., such that in this way an average cycle time can be maintained. In one embodiment, the second value is determined as a proportion of the first value, e.g., 75%, 125%, etc. In one embodiment, a first value may be selected from a first range (e.g., defined by a first minimum limit and a first maximum limit) and a second value may be selected from a second range different than the first range (e.g., defined by a second minimum limit and a second maximum limit that differ from the first maximum and minimum limits). Those of ordinary skill in the art will appreciate any number of methods for generating or determining a random number or set of numbers.

In one embodiment, the operational or performance parameters of the controller 14, e.g., the preset list of values, probabilistic biases, upper and lower limits, etc., are automatically altered depending on the total length of compression therapy given to a patient. For example, the system 10 may utilize a first value or set of values for one or more parameters at the start of therapy, and a second value or set of values after a certain amount of time has elapsed. Further values or sets of values may be additionally used such that a progression in the therapy can be carried out.

Advantageously, since the embodiments described herein do not require any special features or components, the currently disclosed systems are compatible with, or can otherwise utilize existing components from virtually any known or discovered compression therapy systems. That is, existing, commercially-available inflatable garments and/or fluid conduits/tubes (including single or multiple lumen) can be used with no change, which provides extensive backwards compatibility. It is noted that the current embodiments are applicable to systems having garments with any number of chambers, e.g., a single chamber as illustrated in FIG. 3, or multiple chambers such as disclosed in U.S. Pat. No. 6,080,120 or United States Patent Publication No. 2015/245976, which patent references are hereby included by reference in their respective entireties. Likewise, the current embodiments should be readily applicable to future versions of inflatable garments as well. It is also noted that the embodiments disclosed herein can be used with existing garments for any area of the body, e.g., calf, thigh, foot, etc. Additionally, existing actuator/pump hardware and designs may also be reused from current or past systems or the most part, as these systems would only need to be modified to include a controller that controls operation (e.g., via software instructions) of the existing actuator/pumping mechanism in accordance with the embodiments discussed herein.

As discussed herein, current knowledge in the field indicates that 48s is a deflated time useful to the vast majority of patients undergoing calf compression therapy. Accordingly, in some embodiments, the maximum limit for the deflated time is set at about 48s. However, it is to be appreciated that other maximum limits may be utilized. In some embodiments, the maximum limit for the deflated time is selected from the range of 30 to 60 seconds, and in further embodiments is selected from between 40 to 50 seconds. The minimum limit may be set to prevent compressions from occurring too often, as this may disruptive to the patient and/or decrease the effectiveness of treatment if the patient's veins have insufficient time to refill between compressions. In one embodiment, the lower limit for the deflated time is selected from the range of 10 to 40 seconds, while in a further embodiment is selected from between 20 to 30 seconds. It is of course to be noted that the time ranges given herein above and below are recommended primarily with respect to the current inventors' knowledge of existing foot, calf, or calf-and-thigh garments, and that other body parts or anatomical areas (or even these parts and areas) may benefit from other lengths of time.

The inflated time for each cycle may be any selected time, e.g., 12s as typically used in commercial embodiments for calf garments. However, it is also noted that the aforementioned randomization techniques may be applied additionally, or alternatively, to the inflated time if so desired (e.g., subject to minimum and maximum limits, as discussed herein, such as a minimum limit of about 3s to ensure sufficient time for the actuator/pump to be completely actuated and thereby full pressurization achieved). It is also noted that the inflated time for a cycle may be variable in response to the randomized length of the deflated time of that cycle or previous or subsequent cycles. For example, the inflated time in one embodiment may be shortened or lengthened following or preceding a relatively shorter randomized deflated time, or shortened or lengthened following or preceding a relatively longer deflated time. In one embodiment, the entire cycle time (deflated time plus inflated time) may have a minimum cycle length and/or a maximum cycle length. In one embodiment the minimum cycle length is at least 35 seconds. In one embodiment the maximum cycle length is less than 90 seconds. Again, these lengths of time are intended to be non-limiting recommendations helpful to assist in implementation of the currently disclosed embodiments, and that any other length of time may be used. It is of course to be appreciated that the cycle length may be randomized by the embodiments disclosed herein and the deflated time determined by subtracting out the inflated time.

Figure 7:
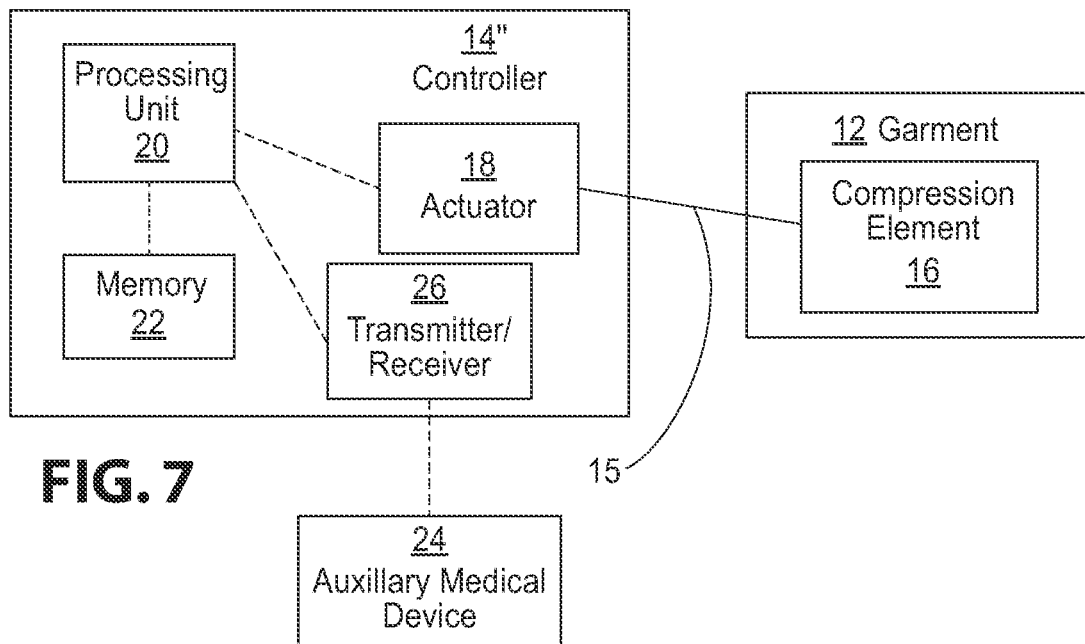
FIG. 7 schematically illustrates a compression therapy system according to another embodiment disclosed herein.

In some embodiments, the performance parameters and/or operation of the controller 14 is/are influenced by one or more auxiliary medical devices and/or variables monitored by an auxiliary device. For example, a system 10" is illustrated in FIG. 7 in which a controller 14" is in communication with an auxiliary device 24, e.g., via a transmitter/receiver 26, which may be any wired or wireless communication device or technology, such as WiFi, infrared, RFID, Bluetooth, Ethernet, etc. It is noted that the controller 14" otherwise resembles the controller 14 and that any discussion of the controller 14 applies to the controller 14".

The variables monitored by the auxiliary medical device 24 may be external or exclusive to the patient, such as ambient room temperature, time of day, etc. Alternatively, the monitored variables may be internal or inclusive to the patient, such as venous pressure, heart rate, detected movement, etc. In one embodiment, the auxiliary device 24 is a piece of diagnostic equipment configured to screen for DVT or other medical conditions. To this end, the auxiliary medical device 24 may be any measuring, sensing or monitoring device for measuring one or more parameters or variables. Alternatively, the auxiliary medical device 24 may be providing some other therapy to the patient and the controller 14" may be arranged to synchronously, complementarily, simultaneously, and/or communicate and/or interact sequentially with the auxiliary device 24. For example, performance parameters of the controller 14" may be at least partially influenced, set, or defined by operation of the auxiliary device 24 and/or the measured results of monitored variables. In one embodiment, the operation and/or accuracy of measurement of the auxiliary device 24 would be impacted if the actuator 18 were simultaneously running, and therefore, the controller 14" is arranged to conduct deflation intervals during operation of the auxiliary device 24 and/or to extend the length of the deflation intervals as necessary so that compression does not occur until after operation of the auxiliary device 24 ceases. Advantageously, since a constant fixed interval is not used for every cycle, the randomization techniques discussed herein can account for a potentially large degree of error in measurement of the monitoring variables and therefore the instrument or sensor doing the monitoring does not have to be highly accurate or finely calibrated. In one embodiment, the performance parameters of the controller 14 are modified by the controller 14 detecting the type, model, manufacturer, or style of the garment 12, the conduit 15, and/or the actuator 18, e.g., such as with RFID as described in U.S. Pat. No. 6,884,255, which patent is hereby incorporated by reference in its entirety.

Figure 8:
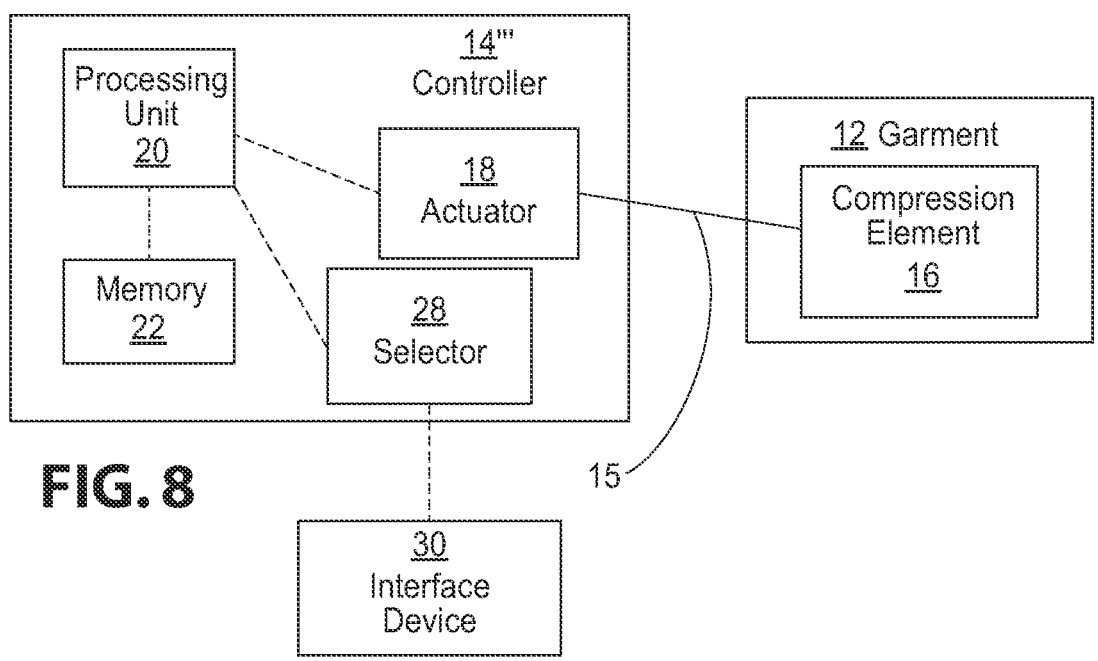
FIG. 8 schematically illustrates a compression therapy system according to another embodiment disclosed herein.

As shown in the embodiment of FIG. 8, a system 10' may optionally include a selector 28 arranged to enable a user to select, define, influence, or input different modes of operation and/or performance parameters of a controller 14" (e.g., the preset list of deflated times, inflated times, probabilistic bias, upper and lower limits, etc.). Similar to the controller 14", the controller 14" otherwise resembles the controller 14 and any discussion of the controller 14 is applicable to the controller 14".

The selector 28 may be arranged as a knob, dial, switch, button, lever, etc., actuation or activation of which enables a user to change a mode of operation of the controller 14". In one embodiment, the selector 28 may be a separate device that is in wired or wireless (e.g., via WiFi, infrared, RFID, Bluetooth, Ethernet, etc.) communication with the controller 14", which enables a user to alter the performance of the controller 14". Via the selector 28, the user may be able to alter the maximum and/or minimum limits of randomization, set whether or not fixed intervals are interspersed among randomized intervals and/or the number of randomized cycles before a fixed interval, toggle the system to operate in accordance to any randomization embodiment discussed herein, etc. The modes of operation selectable by the user may be preset or predetermined profiles, e.g., saved into the memory 22. In one embodiment, the selector 28 may be arranged to turn off randomization, such that the system may return to a traditional fixed interval mode of operation if desired.

A single selector may be arranged to either collectively or individually change multiple performance parameters of the controller 14, or multiple selectors may be included for individually setting or controlling multiple different variables, e.g., a first selector may be included to enable a user to change the upper limit and a mode selector may be included to enable a user to independently change the lower limit. In one embodiment, the selector 28 is arranged to receive an input from the user, e.g., via a keyboard, mouse, touchscreen, etc., or other input or interface device 30, which lets the user specifically define the desired performance parameters. In one embodiment, the mode of operation is selectable between a first mode that has a relatively short deflated time (e.g., around 15-20s for the patient population of FIG. 2) that can be selected by a user if it is believed the patient is at high risk of venous reflux and/or DVT, and a second mode that has a relatively longer deflated time (e.g., around 48s for the patient population of FIG. 1).

Table 1 below is included as a hypothetical example of a set of randomized cycle time values according to one specific, non-limiting embodiment. More specifically, Table 1 includes a listing of two hundred and fifty-five random values, which corresponding respectively to a set of two hundred and fifty-five sequential operating cycles (i.e., deflated time+inflated time) that may be used in one embodiment. In this embodiment, the values of Table 1 have been randomly generated between a maximum limit of 60s and a minimum limit of 37s (e.g., between a maximum deflated time of 48s and a minimum deflated time of 25s, assuming a 12s inflated time for each cycle). The results of Table 1 are also included in the form of a radar plot in FIG. 9, which is discussed in more detail below.

TABLE 1

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| 41 | 50 | 55 | 57 | 58 | 59 | 49 | 54 | 57 | 48 | 54 | 57 | 58 | 59 | 49 | 54 | 47 | 53 | 56 | 58 | 49 | 54 | 47 | 43 | 41 | 50 | 45 | 42 | 41 | 40 |
| 50 | 55 | 47 | 53 | 56 | 48 | 44 | 42 | 51 | 55 | 57 | 58 | 49 | 44 | 52 | 56 | 58 | 49 | 44 | 52 | 56 | 48 | 44 | 41 | 50 | 45 | 52 | 56 | 48 | 54 |
| 47 | 43 | 51 | 45 | 42 | 41 | 50 | 45 | 52 | 46 | 43 | 51 | 45 | 52 | 46 | 53 | 46 | 43 | 51 | 55 | 57 | 48 | 54 | 57 | 58 | 49 | 54 | 57 | 48 | 44 |
| 52 | 56 | 58 | 59 | 49 | 54 | 57 | 58 | 59 | 58 | 57 | 49 | 54 | 47 | 43 | 51 | 55 | 47 | 43 | 52 | 56 | 48 | 54 | 46 | 53 | 46 | 43 | 41 | 50 | 55 |
| 47 | 43 | 41 | 40 | 39 | 50 | 55 | 57 | 48 | 54 | 47 | 53 | 46 | 53 | 46 | 53 | 56 | 58 | 59 | 58 | 49 | 44 | 52 | 46 | 53 | 46 | 43 | 41 | 40 | 50 |
| 45 | 42 | 51 | 55 | 57 | 58 | 59 | 58 | 57 | 60 | 49 | 44 | 42 | 41 | 50 | 45 | 52 | 56 | 58 | 59 | 49 | 44 | 42 | 51 | 55 | 47 | 53 | 46 | 43 | 41 |
| 40 | 39 | 38 | 37 | 50 | 45 | 42 | 41 | 50 | 55 | 57 | 48 | 44 | 42 | 51 | 45 | 42 | 51 | 45 | 52 | 56 | 58 | 49 | 44 | 42 | 41 | 40 | 39 | 50 | 55 |
| 47 | 43 | 51 | 45 | 42 | 51 | 45 | 42 | 51 | 55 | 47 | 53 | 57 | 58 | 49 | 44 | 52 | 46 | 43 | 41 | 40 | 39 | 50 | 45 | 52 | 46 | 53 | 56 | 48 | 54 |
| 57 | 48 | 54 | 47 | 53 | 56 | 48 | 44 | 52 | 46 | 53 | 56 | 48 | 44 | 42 | | | | | | | | | | | | | | | |

The values of Table 1 have a sum of 12,619s, such that the 255 cycles of Table 1 would enable operation of a compression therapy system for a total of 210 minutes and 19 seconds, with an average cycle length of 49s. In comparison, a traditional system having a fixed 60 second cycle time would only cycle 210 times in this same time period. Accordingly, the embodiment of Table 1 would provide approximately 21% more cycles than a traditional 60s fixed interval system over the same time period.

It is furthermore noted that although the embodiment of Table 1 has an average cycle length of 49s, the treatment received by patients would not be the same as if a fixed cycle length of 49s were used. In addition to the other advantages discussed herein, one further advantage of the randomization techniques disclosed herein that can be better appreciated in view of FIG. 9, which graphically represents the values of Table 9, is that as a result of randomization, sets of consecutive values will create and/or follow various different types of sequences (alternatively referred to herein as patterns) that may yield beneficial effects for some patients. For example, in one embodiment, a subset of consecutive random values may follow a pattern in which each subsequent value is longer than the previous. In one embodiment, a subset of consecutive random values may follow a pattern in which each subsequent value is shorter than the previous. In one embodiment, a subset of consecutive random values may follow a pattern in which the values alternate or oscillate between relatively long and relatively short times.

As noted above, FIG. 9 is a radar plot graphically illustrating the cycle time values of the 255 cycles tabulated in Table 1 and is provided to help illustrate some sequences or patterns that may be beneficial to patients during compression therapy. For example, several instances of various types of patterns have been identified in FIG. 9 with the following alphabetic identifiers: 'A' identifies areas of progressively increasing cycle length; 'B' identifies areas of progressively decreasing cycle length; 'C identifies areas of relatively short cycle times surrounded by areas of relatively long cycle times; 'D' identifies areas having a group of multiple cycle times that all fall below a certain threshold; and 'E' identifies areas having a group of multiple cycle times that all fall above a certain threshold. It is believed by the current inventors that some patients may benefit from certain types of sequences, or that certain types of adjacent sequences (e.g., sequence A followed by sequence B, alternatingly areas of sequences D and E, etc.), may yield synergistic effects that the human body responds to even more favorably than conventional fixed intervals. It is noted that not all instances of the aforementioned sequences are identified in FIG. 9 and further, that these types of sequences are non-limiting examples for the purpose of discussion only and other sequences are present and may be found to be beneficial to patients undergoing compression therapies.

In some embodiments, forced sequencing is utilized when generating the randomized values. By "forced sequencing" it is meant that one or more subsets of sequential values are arranged to follow a particular type of sequence or pattern, e.g., any of the above-discussed sequences. In other words, groups or subsets of the values may be purposely selected to follow a predetermined pattern, or the mathematical formula utilized to generate the values may be modified based on the result of one or more previous cycles in order to guarantee certain sequencing.

Figure 10:
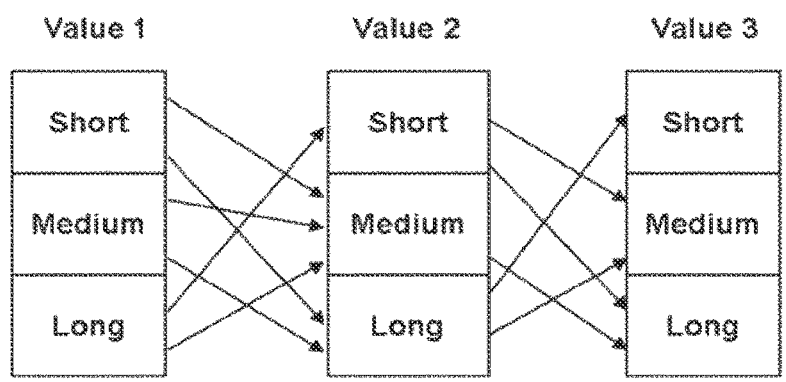
FIG. 10 is a diagram to facilitate explanation of an example of forced sequencing that can be employed to randomly generated values.

One embodiment making use of forced sequencing can be appreciated in view of FIG. 10, which is not intended to be limiting, and instead included for the sake of discussion only. In this embodiment, the values can be in one of three ranges: short, medium, or long. For example, short could correspond to a cycle time of 45-50s, medium to 50-55s, and long to 55-60s. A first random value ("Value 1") is selected and/or generated for the first cycle via any desired method (e.g., the controller 14 of the system 10 using any of the methods disclosed herein). This first value is then used to influence the next selected/generated value for the subsequent cycle as indicated by the arrows between Value 1 and the second value ("Value 2"), and between Value 2 and the value for the third cycle ("Value 3"). In this example, if the first value is designated as short, then the second value must be medium or long. Alternatively, if the first value is medium length, then the second value must be medium or long; while if the first value is long, then the second value must be medium or short. Likewise, a short second value can be a medium or long third value, a medium second value can only result in a long third value, and a long second value can be either a short or medium length third value.

The forced sequencing process can repeat as needed for any number of cycles, and those of ordinary skill in the art will appreciate that any pattern or sequence can be forced or imposed on the values in this way. It is also noted that fixed values may be interspersed among the randomly generated values, e.g., a randomly generated short value could trigger the next value to be a predetermined fixed value. Forced sequencing may be accomplished in some embodiments by altering the minimum and/or maximum limits for the random number selection/generation, or by performing a mathematical comparison on the randomly selected/generated value and continuing to select/generate values until a value falls into the permitted range. Advantageously in this way, a user is able to achieve a defined and repeatable performance characteristic by imposing some degree of control on the operation of the system, but while still benefiting from randomization as disclosed herein. In one embodiment, forced sequencing may be used to impose what is perceived by users to be increased "randomness", but which is not truly random. For example, in a random sampling, it is likely that repeated values may occur, e.g., the same number may be selected two or more times in a row. Despite repeated values occurring randomly, such repeated values do not "appear" to be random. That is, users may perceive a bias in even a perfectly random system if certain values are repeated more often than other values (e.g., the sequence {35, 35, 35, 35, 51, 35, 35, 35} may be randomly generated, but does not appear to be random due to the frequency that '35' is selected). Accordingly, forced sequencing can be used to prevent values from repeating too frequently (e.g., the same number cannot be selected twice in a row, the same number cannot be selected 'x' number of times in a group of 'y' cycles, etc.).

Figure 11:
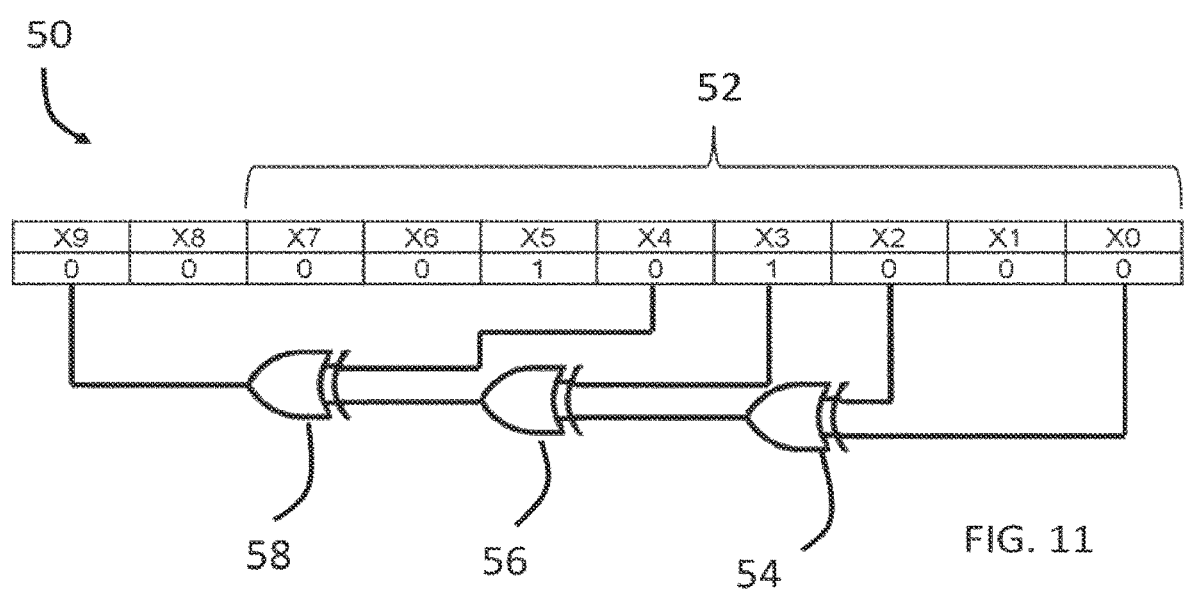
FIG. 11 is a diagram of linear feedback shift register arranged to generate a sequence of random values.

FIG. 11 depicts a linear feedback shift register 50 according to one embodiment that may be utilized to generate random values. Advantageously, a linear feedback shift register can generate a sequence of random numbers using a minimal amount of memory or circuitry. It also generates a list or sequence of pseudorandom numbers that does not repeat until the sequence is completely generated, then automatically repeats this full sequence of numbers. It can also be arranged to create a desired, or predictable, sequence by setting the initial values of the register.

The linear feedback shift register 50 has ten bits X0-X9 (thus, as a bit, each of X0-X9 can take the value of 0 or 1). In this embodiment, the first eight bits X0- X7, create a value in base-2, also designated with the reference numeral 52. The random binary value 52 may be converted to base-10 if necessary (e.g., via the processing unit 20). The sequence is sampled by using the lower eight bits from the register for the randomized value 52, providing 256 potential values, however the shift register 50 itself does not repeat its sequence until after 1,023 cycles. The bits X8 and X9 are used for randomization purposes as discussed below, and can initially be preloaded with difference values to allow differing sequences to be generated.

In order to randomize the binary value 52, the shift register 50 includes three exclusive OR ("XOR") gates, designated as XOR gates 54, 56, and 58. Each of the gates 54, 56, and 58, is arranged to generate an output dependent on the state of the inputs and this is used to influence the register values. The gate 54 is arranged with inputs from bits X0 and X2; the gate 56 with inputs from bit X3 and the output of the gate 54; and the gate 58 with inputs from the bit X4 and the output of the gate 56. Those of ordinary skill in the art will recognize any number of other arrangements that circuitry utilizing a shift register may take in order to procedurally generate sequences of numbers.

According to the illustrated embodiment, after each time the random binary value 52 is determined (e.g., and used as the randomized cycle time, deflated time, etc.), the value of the bit X9 is calculated by the XOR gates 54, 56, and 58 and set as the output of the third XOR gate 58. The values of the other bits (X0-X8) are determined by shifting the values of bits X1-X9 to the next lower bit (e.g., the bit X8 takes the previous value of the bit X9, the bit X7 takes the previous value of the bit X8, etc.). The value from the bit X0 when shifted logically to the next lower bit can be discarded in this example. Thus, the linear feedback shift register 50 would shift from the 0000101000 (80 in decimal notation) shown in FIG. 11 to 1000010100 (53 in decimal notation), with the randomized binary value 52 now equaling 00010100 (or 20 in decimal).

The new value of 1 for the bit X9 would be generated as follows: the gate 54 would generate a 0 due to the original two inputs from X0 (0) and X2 (0); the gate 56 would generate a 1, due to the original two inputs from X3 (1) and 54 (0); and the gate 58 would generate and fill the bit X9 with the new value of 1 as a result of the inputs from X4 (0) and the gate 56 (1). The resulting values in the register 50 can be scaled and processed as required for use within the system. Other modes of operation to construct the circuit like that in FIG. 11 and utilize the data provided by the shift register 50 are clearly possible to those skilled in the art.

Figure 12:
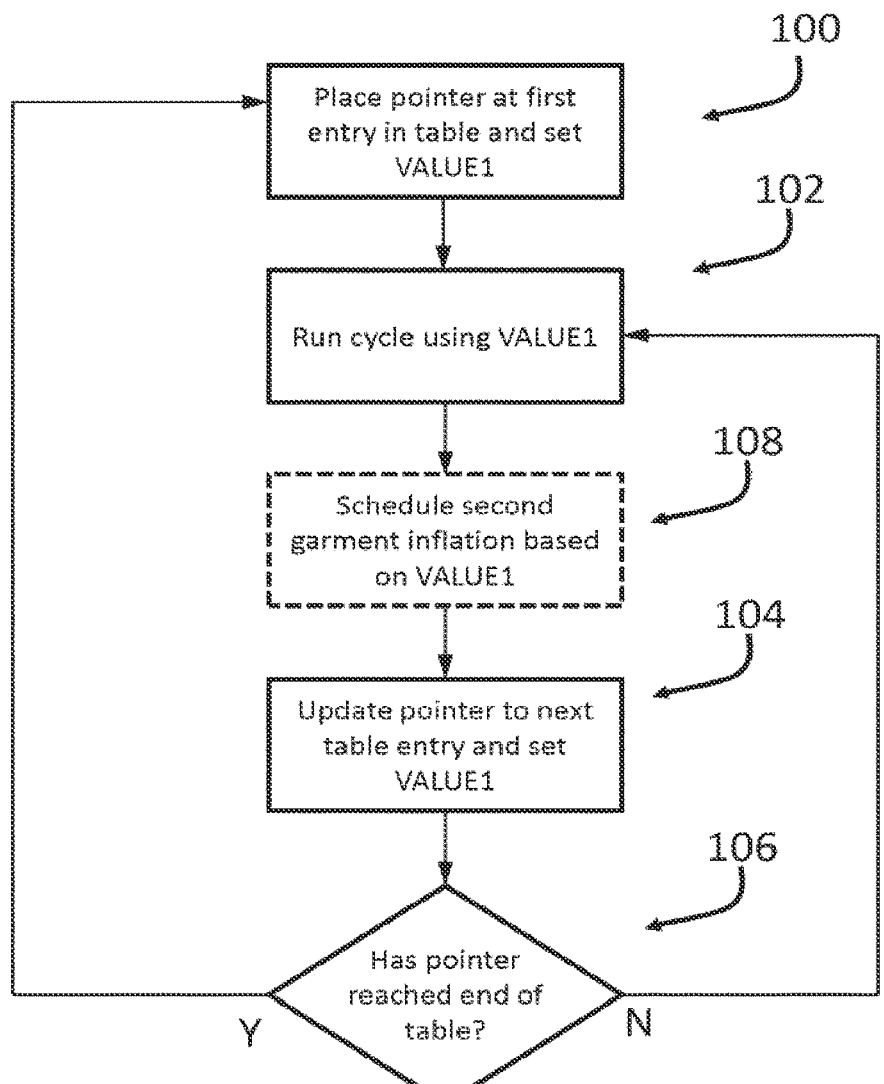
FIG. 12 is a flowchart showing a method of operating a compression therapy system according to one embodiment disclosed herein.

FIG. 12 is a flow chart showing one mode of operation of the controller 14, more specially, in which the randomized values are obtained by progressing a pointer through a pre-generated list or table. In this embodiment, the random value, "VALUE1", is set to the first value in the table in a first step 100. A cycle is then run in a step 102 utilizing VALUE1 to set the cycle length, deflated time, or other parameter. Thereafter, the pointer is updated to the next table entry, and VALUE1 is set to the value stored in this next entry according to a step 104. The system, e.g., the system 10, then determines, e.g., utilizing the processing unit 20, whether or not the end of the table has been reached in a step 106. If the answer is yes, the pointer is reset to the first entry in the table, thereby repeating the process from the step 100. If the answer to step 106 is no, then the value of VALUE1 is acceptable for use in a cycle and the process is repeated from step 102. The process continues continuously or for a set number of cycles or until terminated by user input or command.

If two garments are in use (e.g., the system 10'), a step 108 may optionally occur before, during, or after the step 102 in which the timing of inflation of the second garment is scheduled to occur at a time that is aligned with VALUE1. In other words, in step 108 the inflation of a second garment is set or scheduled to occur during the same period (although not necessarily for the same length of time) that a first garment is deflated. If two garments are used, it should be understood that the second garment operates in the same manner as depicted in FIG. 12, but with VALUE1 referring instead to the second and subsequent garment inflations and step 108 referring to the first garment.

Figure 13:
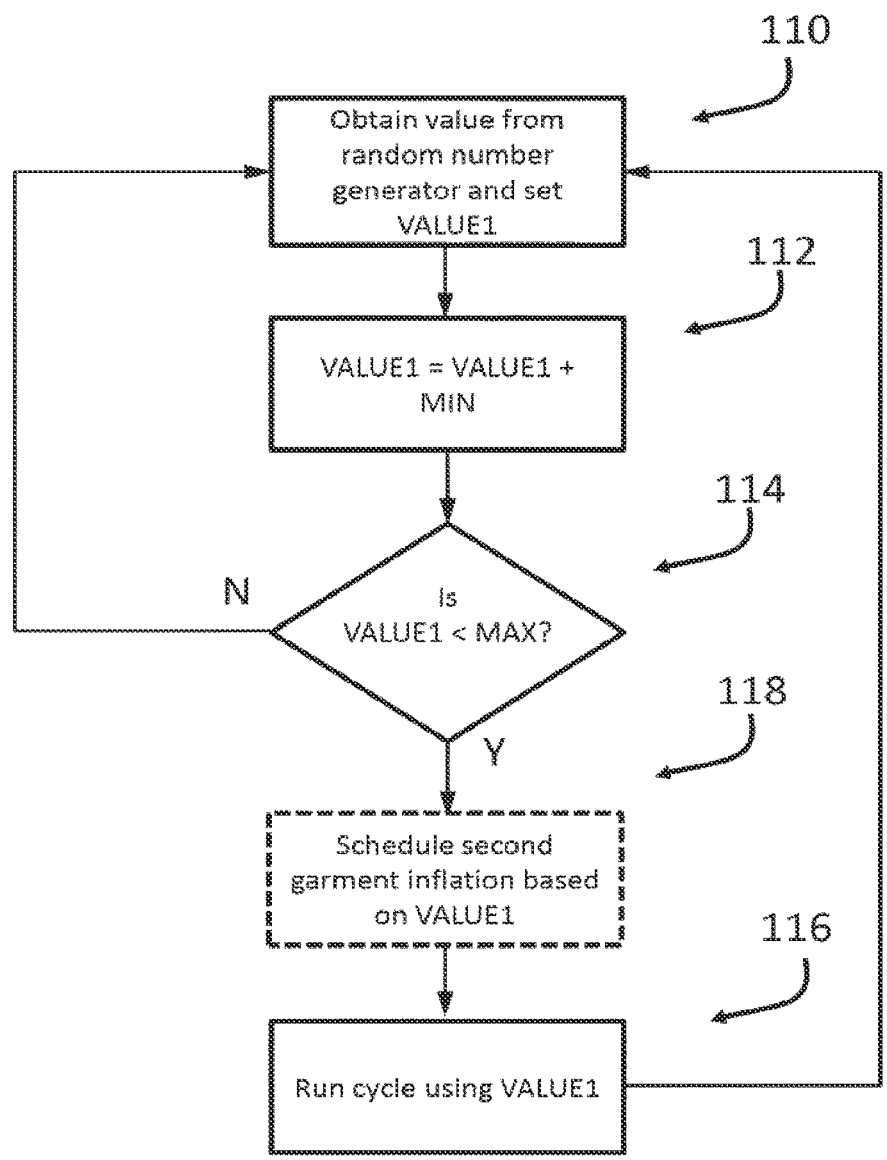
FIG. 13 is a flowchart showing a method of operating a compression therapy system according to another embodiment disclosed herein.

Another mode of operation can be appreciated in view of the flow chart of FIG. 13. In this embodiment, the randomized values (again, "VALUE1") are generated as needed or on-the-fly. Additionally, in this embodiment, the values are only selected if the time is between a minimum limit, "MIN", and a maximum limit, "MAX". In a first step 110, a random number generator generates a random value, VALUE 1 (e.g., via any of the above techniques, methods, manners, or embodiments). If VALUE 1 in the step 110 can be been generated between the limits of MAX and MIN (e.g., via a rand or random software function), then the steps 112 and 114 can be skipped. Alternatively, if the randomized value is generated via some other manner, e.g., via a linear shift register as discussed with respect to FIG. 11, then the method of FIG. 13 proceeds to the step 112 in which MIN is added to VALUE1 in order to update the value of VALUE1, and guarantee the VALUE1 will be greater than or equal to MIN when used. In the step 114, it is checked (e.g., via the processing unit 20), whether VALUE1, updated in the step 112, is greater than MAX. If the answer is no, the process starts over from the step 110 and a new value for VALUE1 is selected. If the answer in the step 114 is yes, the cycle is run using the VALUE1. Similar to the embodiment of FIG. 12, a step 118 may optionally occur in the event that two garments are utilized in order to ensure one garment is inflated while the other is deflated. It should be clear to those ordinarily skilled in the art that additional logical tests (not shown in FIG. 13 for simplicity purposes) can be readily included to avoid the algorithm becoming permanently stuck in a loop of steps 110-114.

Figure 14:
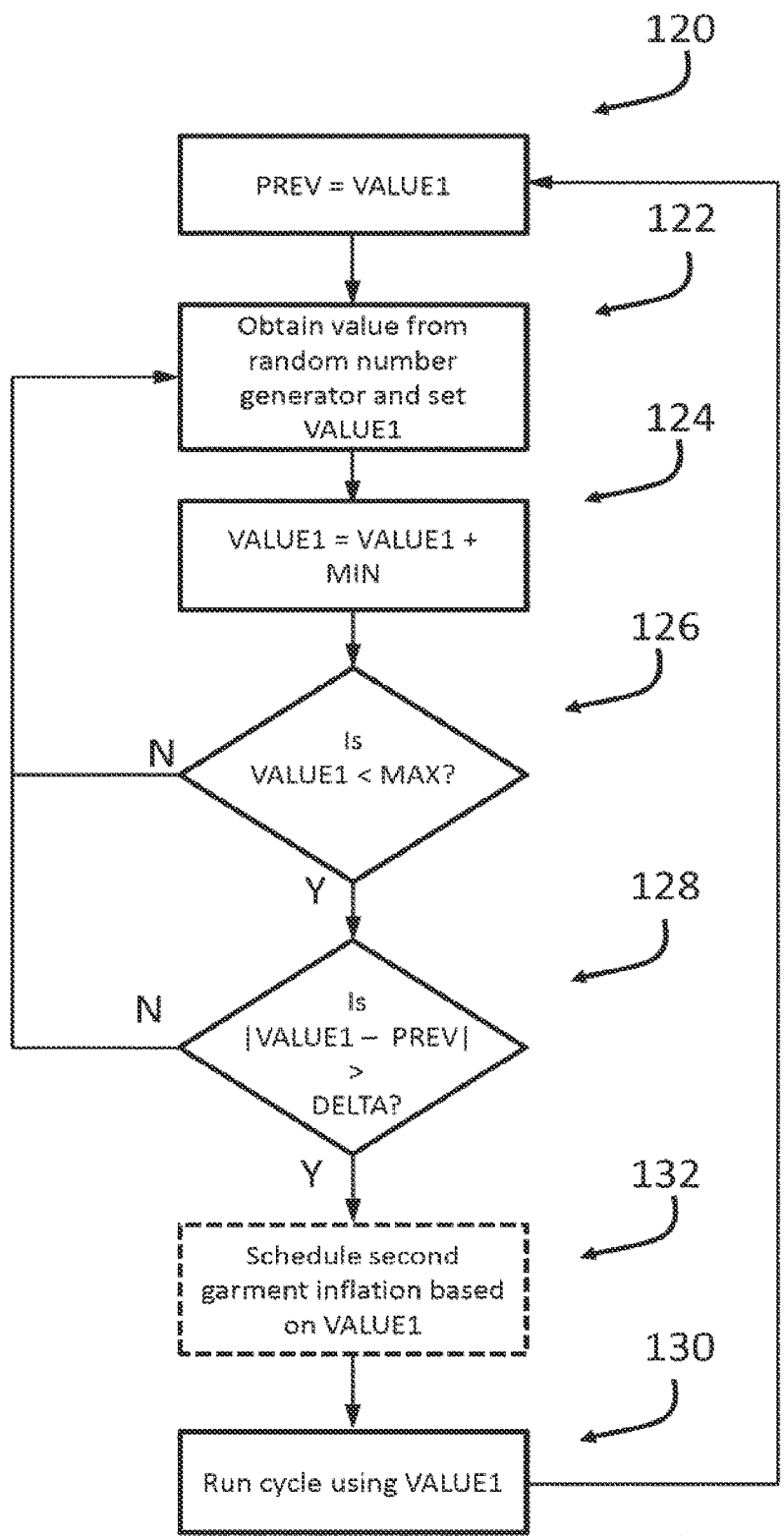
FIG. 14 is a flowchart showing a method of operating a compression therapy system according to another embodiment disclosed herein.

FIG. 14 illustrates another embodiment in which the random value (again, "VALUE1") is generated as needed or on-the-fly during operation of the system. In a first step 120, a parameter PREV is set as being equal to VALUE1 as a pre-load or seed to allow the initialization of the process (akin to the values in FIG. 11). Since VALUE1 ultimately represents the randomized value used in the cycle, PREV is effectively set to store the previous time used. A step 122 then occurs, resembling the step 110, in which a random number generator is used to select a random number. A set of steps 124 and 126 then occur similar to the steps 112 and 114, and may likewise be skipped depending on how VALUE1 in the step 122 is generated. If the answer to the step 126 is yes, then the system determines whether there is a sufficient degree of differentiation between VALUE1 and PREV. For example, this can be mathematically determined by comparing the absolute value of the difference between VALUE1 and PREV to a predetermined threshold, "DELTA". For example, DELTA can be modified between cycles to enforce forced sequencing as discussed above. By setting DELTA equal to zero, it can be ensured that a value does not repeat. The step 118 can be optionally skipped, or DELTA set to any negative number if a degree of differentiation between subsequent cycles is not desired. If the answer to the step 128 is no, then a new value is randomly generated and VALUE1 is set to this value. If the answer to the step 128 is yes, then the VALUE1 is acceptable and can be used during the next cycle as indicated in the step 130. If two garments are being used, a step 132 may be included similar to the steps 108 and 118 discussed above. As described above, additional logical tests (not shown in FIG. 14 for simplicity purposes) can be included to avoid the algorithm becoming permanently stuck in a loop of steps 122-128.

The parameters of current compression therapy systems are often adjusted by the medical practitioner giving the therapy in order to improve patient comfort and compliance. To this end, in some embodiments, the controller 14 is arranged to automatically modify certain parameters of the compression therapy in response to the use of randomized values. In one embodiment, the controller 14 is arranged to modify the maximum pressure exerted by the compression element 16 for different cycles during use of the system 10. Oppositely, it is noted that the randomized value may be affected by the pressure exerted by the compression element 16. For example, the pressure may be selectable by a user or other variable, and the selected pressure utilized to set the maximum and/or minimum limits of the randomization as discussed herein. In one embodiment, the compression pressure of the compression element 16 and/or the inflation pressure in the chamber 16' is at least about 25 mmHg and in one embodiment up to about 65 mmHg, although it should be appreciated that other pressures may be clinically advantageous depending on with which anatomic site the currently disclosed embodiments are used.

In one embodiment, e.g., if the therapy becomes more effective in terms of increased volume of venous flow as a result of an increased number of compressions per unit time as discussed herein, it is possible that sufficient performance for that patient can be achieved even after a corresponding reduction in the pressure exerted by the compression element 16. In other words, the controller 14 can automatically provide a change in pressure that is dependent on the value of the current cycle time selected and/or one or more previous cycle times. That is, if there are a number of shorter cycles, these could be associated with a slightly reduced pressure level as the faster repetition associated with these shorter cycles provides an augmented flow. In this way, it is possible that the compression pressure experienced by the patient can be reduced, improving comfort for some patients. Conversely, if there are a number of longer cycle times resulting in a larger period between compressions then it may be desirable to have an increased pressure to ensure a sufficient level of augmented blood flow.

The above-described interrelationship between cycle time and compression pressure may be utilized continuously during operation of the system 10 or selectively for only particular cycles. In one embodiment, the user or medical professional operating the system 10 can operate a switch (hardware or software) to selectively turn this mode on or off or use any input or interface device (e.g., keyboard, mouse, touchscreen) to set conditions under which this functionality is enabled. In one embodiment, the pressure is set with respect to the randomized values selected as discussed herein automatically upon a sensed parameter or condition, such as when the patient is detected as being in a specific physical position (e.g., lithotomy with legs raised and hence an improved level of venous return), based on the time of day (e.g., night time when the patient is trying to sleep), etc.

Figure 15:
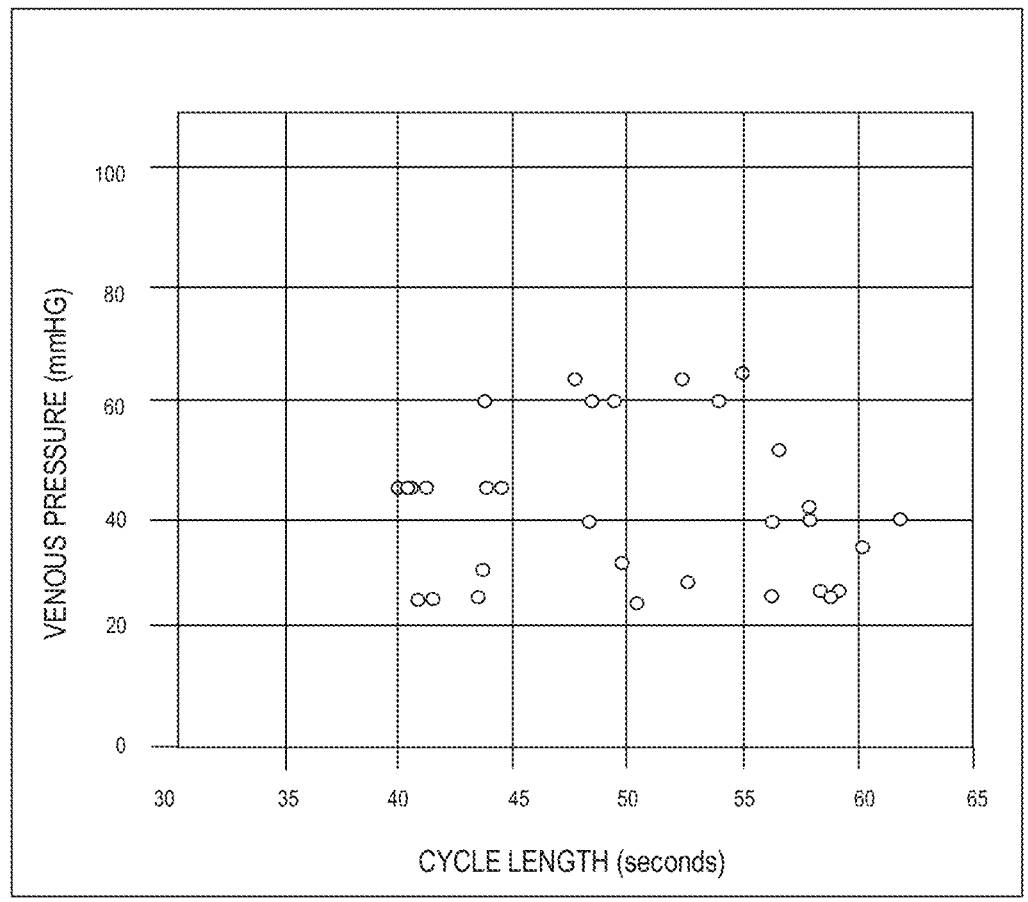
FIG. 15 is a diagram illustrating cycle lengths vs. the venous pressure for thirty-one random compression cycles.

FIG. 15 is a diagram illustrating cycle lengths (e.g., in seconds) vs. venous pressure (e.g., in mmHG) for thirty-one random compression cycles.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. An apparatus for promoting vascular circulation, comprising:
    a garment configured to at least partially surround an anatomical structure of a patient;
    a compression element coupled to the garment and configured to compress at least a portion of the anatomical structure when the compression element is actuated; and
    a controller configured to communicate with an actuator, communicate with the compression element via a conduit, and selectively actuate the compression element over a plurality of cycles in a sequence;
    wherein each cycle has an actuated time during which the compression element is configured to inflate and exert a first pressure, and an unactuated time during which the compression element is configured to change from the first pressure to a second pressure different than the first pressure,
    wherein the plurality of cycles has a plurality of actuated times and a plurality of unactuated times, wherein each unactuated time of the plurality of unactuated times in the sequence of the plurality of cycles is random and constantly variable such that no pair of sequential deflated times has the same length,
    wherein the controller is configured to use one or more random values in determining the unactuated time of one or more of the cycles, and wherein the random values are pseudorandomly generated by a mathematical algorithm.

2. The apparatus of claim 1, wherein the random values are selected from within a range defined between a minimum limit and a maximum limit, and wherein the range is variable between different cycles.

3. The apparatus of claim 2, wherein a parameter is utilized by the controller in determining the range.

4. The apparatus of claim 3, wherein the parameter is related to the anatomical structure; the patient or the patient's condition or status; an ambient environment in which the anatomical structure or the patient is located during use of the apparatus; a medical device monitoring the patient; a detected type, model, manufacturer, or style of the garment; or a combination including at least one of the preceding.

5. The apparatus of claim 1, wherein the controller determines a set of random values for a set of cycles and arranges the set of random values in a forced sequence.

6. The apparatus of claim 5, wherein for a number of cycles the forced sequence is increasing in value; decreasing in value; oscillating between relatively greater and relatively lower values; within a set deviation from a threshold value, a minimum value, or a maximum value; or a combination including at least one of the preceding.

7. The apparatus of claim 1, wherein the anatomical structure is a calf, a thigh, a foot, a leg, an arm, a hand, an abdomen, a buttocks, a portion of at least one of the foregoing, or combination including at least one of the preceding.

8. The apparatus of claim 1, wherein the compression element comprises an inflatable chamber, and wherein the actuator is a pump configured to inflate and deflate the inflatable chamber.

9. An apparatus for providing compression therapy to an anatomic structure of a patient, comprising:
- a compression element configured to exert a first compression pressure and a second compression pressure different than the first compression pressure;
- a controller configured to selectively actuate the compression element over a plurality of cycles in a sequence, each cycle having an actuated time during which the compression element is exerting the first compression pressure and an unactuated time during which the compression element is exerting the second compression pressure,
- wherein the controller constantly variably sets the unactuated time for each cycle of the plurality of cycles such that the unactuated time is not the same for any set of two sequential cycles in the plurality of cycles, and
- wherein the random values are pseudorandomly generated by a mathematical algorithm.

10. A method for using a pump to inflate and deflate a chamber of a compression garment configured to be positioned about an anatomic structure, the method comprising the steps of:
- selectively inflating and/or deflating the chamber over a plurality of cycles in a sequence, wherein each cycle has an inflated time and a deflated time, wherein the plurality of cycles has a plurality of inflated times and a plurality of deflated times, wherein each deflated time of the plurality of deflated times in the sequence of the plurality of cycles is random and constantly variable such that no pair of sequential deflated times has the same length; and
- assigning one or more random values for the deflated times of one or more of the cycles,
- wherein the random values are pseudorandomly generated by a mathematical algorithm.

11. The method of claim 10, wherein the random values are selected from within a range defined between a minimum limit and a maximum limit, wherein the range is variable between different cycles.

12. The method of claim 10, wherein a parameter is utilized in determining the range, and wherein the parameter is related to the anatomical structure; the patient or the patient's condition or status; an ambient environment in which the anatomical structure or the patient is located during use of the apparatus; a medical device monitoring the patient; a detected type, model, manufacturer, or style of the garment; or a combination including at least one of the preceding.

13. A method for using the apparatus of claim 1, wherein the apparatus is configured to be positioned about an anatomic structure of a person, the method comprising the steps of:
- selectively inflating and/or deflating the compression element of the apparatus over the plurality of cycles.

14. A method for using the apparatus of claim 9, wherein the apparatus is configured to be positioned about an anatomic structure of a person, the method comprising the steps of:
- selectively inflating and/or deflating the compression element of the apparatus over the plurality of cycles.

* * * * *